United States Patent [19]
Lunkenheimer et al.

[11] Patent Number: 5,189,061
[45] Date of Patent: Feb. 23, 1993

[54] (2-CYANO-2-OXIMINOACETYL)-AMINO ACID DERIVATIVES

[75] Inventors: Winfried Lunkenheimer, Wuppertal; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 673,433

[22] Filed: Feb. 22, 1991

Related U.S. Application Data

[62] Division of Ser. No. 551,692, Jul. 10, 1990, Pat. No. 5,026,710, which is a division of Ser. No. 200,084, May 27, 1988, Pat. No. 4,963,548.

[30] Foreign Application Priority Data

Jun. 9, 1987 [DE] Fed. Rep. of Germany ....... 3719227

[51] Int. Cl.$^5$ ..................... C07C 255/61; A01N 37/34
[52] U.S. Cl. ................................... 514/519; 514/521; 514/528; 558/301
[58] Field of Search ................ 558/301; 514/521, 528, 514/519

[56] References Cited

U.S. PATENT DOCUMENTS

| | | | |
|---|---|---|---|
| 3,979,518 | 9/1976 | Klopping | 558/301 X |
| 4,478,848 | 10/1984 | Brandes et al. | 558/301 X |
| 4,782,086 | 11/1988 | Lunkenheimer et al. | 544/386 X |
| 4,841,086 | 6/1989 | Gayer et al. | 558/301 |
| 4,963,548 | 10/1990 | Lunkenheimer et al. | 558/301 X |

FOREIGN PATENT DOCUMENTS

| | | |
|---|---|---|
| 0201999 | 11/1986 | European Pat. Off. |
| 3035145 | 4/1981 | Fed. Rep. of Germany ...... 558/301 |
| 3322010 | 12/1984 | Fed. Rep. of Germany ...... 558/301 |
| 3602243 | 12/1986 | Fed. Rep. of Germany ...... 558/301 |
| 3625497 | 2/1988 | Fed. Rep. of Germany ...... 558/301 |

*Primary Examiner*—Joseph Paul Brust
*Attorney, Agent, or Firm*—Sprung Horn Kramer & Woods

[57] ABSTRACT

Novel fungicidally active compounds of the formula $$R-O-N=C\begin{matrix}CN\\ \\CO-NH\text{-alkylene-}CO-R^1\end{matrix} \quad (I)$$

in which

R represents alkyl, cyanoalkyl or in each case optionally substituted alkenyl, alkinyl, cycloalkyl, cycloalkylalkyl or phenylalkyl, $R^1$ represents the $-OR^2$ or $-NR^3R^4$ groups, and $R^3$ and $R^4$ have special special definitions.

6 Claims, No Drawings

(2-CYANO-2-OXIMINOACETYL)-AMINO ACID DERIVATIVES

This is a division of application Ser. No. 551,692, filed Jul. 10, 1990, now U.S. Pat. No. 5,026,710, which is a division of application Ser. No. 200,084, filed May 27, 1988, now U.S. Pat. No. 4,963,548.

The present invention relates to new (2-cyano-2-oximino-acetyl)-amino acid derivatives, several processes for their preparation, and their use as pesticides, in particular as fungicides.

It has already been disclosed that certain substituted 2-cyano-2-methoximino-acetamides have a good fungicidal activity (cf., for example EP-OS (European Published Specification) 0,201,999 and DE-OS (German Published Specification) 3,602,243). However, the action of these compounds is not always completely satisfactory, particularly at low application rates and concentrations.

New (2-cyano-2-oximinoacetyl)-amino acid derivatives of the general formula (I)

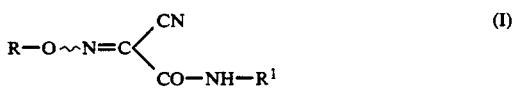

in which

R represents alkyl, cyanoalkyl or in each case optionally substituted alkenyl, alkinyl, cycloalkyl, cycloalkylalkyl or phenylalkyl, $R^1$ represents the —A—COOR$^2$ or —B—CONR$^3$R$^4$ groups, in which A represents an optionally substituted, straight-chain or branched alkylene chain, B represents an optionally substituted, straight-chain or branched alkylene chain, $R^2$ represents substituted alkyl having the following substituents: halogen, hydroxyl, alkoxy, acyloxy, optionally substituted aryl, optionally substituted cycloalkyl and optionally substituted heterocyclyl;

$R^3$ represents substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, in each case optionally substituted aryl, heterocyclyl, cycloalkyl and cycloalkenyl; $R^3$ further represents in each case optionally substituted alkenyl, alkinyl, cycloalkyl, cycloalkenyl, aryl or heterocyclyl, and $R^4$ represents substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, in each case optionally substituted aryl, heterocyclyl, cycloalkyl and cycloalkenyl; $R^4$ furthermore represents in each case optionally substituted alkenyl, alkinyl, cycloalkyl, cycloalkenyl, aryl, heterocyclyl or a polycyclic carbocyclic ring or the —OR$^{IV}$ group, or $R^3$ represents hydrogen or alkyl, and $R^4$ represents substituted alkyl having the following substituents: acyl, hydroxyl, alkylcarbonyloxy, —S(O)$_n$R$^{IV}$, in each case optionally substituted heterocyclyl, cycloalkyl and cycloalkenyl; $R^4$ furthermore represents in each case optionally substituted cycloalkenyl, heterocyclyl or polycyclic carbocyclic rings, represents substituted cycloalkyl where, however, halogen and alkyl may not be present as the only substituents, or represents the —OR$^{IV}$ group, or $R^3$ and $R^4$, together with the nitrogen atom to which they are bound, represent a substituted, monocyclic heterocyclic ring or an optionally substituted bi- or tricyclic heterocyclic ring or spiroheterocyclic ring having 1 to 3 further identical or different heteroatoms, such as oxygen, sulphur or nitrogen atoms, $R^I$ represents hydrogen or optionally substituted alkyl having the following substituents: halogen, in each case optionally substituted aryl, cycloalkyl and cycloalkenyl, $R^{II}$ and $R^{III}$ are identical or different and represent hydrogen or optionally substituted alkyl, having the following substituents: halogen, —COOR$^{IV}$, —CONR$^I$R$^{IV}$, in each case optionally substituted aryl, cycloalkyl and cycloalkenyl; $R^{II}$ and $R^{III}$ furthermore represent alkenyl, alkinyl or in each case optionally substituted cycloalkyl, cycloalkenyl, aryl or heterocyclyl, or, together with the nitrogen atom to which they are bound, represent an optionally substituted heterocyclic ring which may contain further heteroatoms, $R^{IV}$ represents hydrogen, alkyl, aralkyl or acyl, and n represents numbers 0, 1 or 2, have been found.

The compounds of the formula (I) can occur in various geometrical isomers, depending on the arrangement of the substituents on the C=N group (E- or Z-isomers).

The compounds may contain one or more asymmetrical carbon atoms; they can thus also exist as optical isomers (D- and L-configuration), which can arise in various amount ratios. They arise mainly as racemates.

It has furthermore been found that the new (2-cyano-2-oximinoacetyl)-amino acid derivatives of the general formula (I)

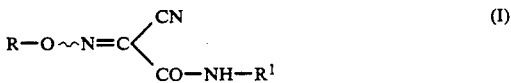

in which

R represents alkyl, cyanoalkyl or in each case optionally substituted alkenyl, alkinyl, cycloalkyl, cycloalkylalkyl or phenylalkyl, $R^1$ represents the —A—COOR$^2$ or —B—CONR$^3$R$^4$ groups, in which A represents an optionally substituted, straight-chain or branched alkylene chain, B represents an optionally substituted, straight-chain or branched alkylene chain, $R^2$ represents substituted alkyl having the following substituents: halogen, hydroxyl, alkoxy, acyloxy, optionally substituted aryl, optionally substituted cycloalkyl and optionally substituted heterocyclyl;

$R^3$ represents substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, in each case optionally substituted aryl, heterocyclyl, cycloalkyl and cycloalkenyl; $R^3$ further represents in each case optionally substituted alkenyl, alkinyl, cycloalkyl, cycloalkenyl, aryl or heterocyclyl, and $R^4$ represents substituted alkyl having the following substituents: halogen, cyano, —COOR$^I$, —CONR$^{II}$R$^{III}$, —NR$^{II}$R$^{III}$, —OR$^{IV}$, —S(O)$_n$R$^{IV}$, acyl, in each case optionally substituted aryl, heterocyclyl, cycloalkyl and cycloalkenyl; $R^4$ furthermore represents in each case optionally substituted alkenyl, alkinyl, cycloalkyl, cycloalkenyl, aryl, heterocyclyl or polycyclic carbocyclic rings or the —OR$^{IV}$ group, or $R^3$ represents hydrogen or alkyl, and $R^4$ represents substituted alkyl having the following substituents: acyl, hydroxyl, alkylcarbonyloxy, $-S(O)_nR^{IV}$, in each case optionally substituted heterocyclyl, cycloalkyl and cycloalkenyl; $R^4$ furthermore represents in each case optionally substituted cycloalkenyl, heterocyclyl or polycyclic carbocyclic rings, represents substituted cycloalkyl where, however, halogen and alkyl may not be present as the only substituents, or represents the $-OR^{IV}$ group, or $R^3$ and $R^4$, together with the nitrogen atom to which they are bound, represent a substituted, monocyclic heterocyclic ring or an optionally substituted bi- or tricyclic heterocyclic ring or spiroheterocyclic ring having 1 to 3 further identical or different heteroatoms, such as oxygen, sulphur or nitrogen atoms, $R^1$ represents hydrogen or optionally substituted alkyl having the following substituents: halogen, in each case optionally substituted aryl, cycloalkyl and cycloalkenyl, $R^{II}$ and $R^{III}$ are identical or different and represent hydrogen or optionally substituted alkyl, having the following substituents: halogen, $-COOR^{IV}$, $-CONR^IR^{IV}$, in each case optionally substituted aryl, cycloalkyl and cycloalkenyl; $R^{II}$ and $R^{III}$ furthermore represent alkenyl, alkinyl or in each case optionally substituted cycloalkyl, cycloalkenyl, aryl or heterocyclyl, or, together with the nitrogen atom to which they are bound, represent an optionally substituted heterocyclic ring which may contain further heteroatoms, $R^{IV}$ represents hydrogen, alkyl, aralkyl or acyl, and n represents numbers 0, 1 or 2, are obtained when a) 2-cyano-2-oximino-acetates of the general formula (II)

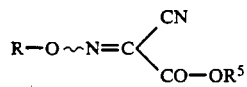  (II)

in which

R has the abovementioned meaning, and $R^5$ represents alkyl, are reacted with amines of the formula (III)

  (III)

in which $R^1$ has the abovementioned meaning, if appropriate in the presence of a diluent and if appropriate in the presence of a base; or b) carboxyl-activated derivatives of carboxylic acids of the general formula (IV)

  (IV)

in which

R has the abovementioned meaning, are reacted with amines of the formula (III)

  (III)

in which $R^1$ has the abovementioned meaning, if appropriate in the presence of a catalyst and if appropriate in the presence of an acid-binding agent and if appropriate in the presence of a diluent; or c) 2-cyano-2-oximino-acetamides of the general formula (V)

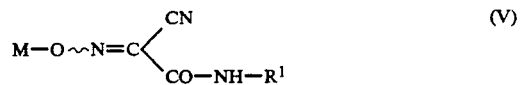  (V)

in which

M represents hydrogen, an alkali metal ion, a protonated tertiary base or a quaternary ammonium ion, and $R^1$ has the abovementioned meaning, are reacted with compounds of the formula (VI)

  (VI)

in which

X represents halogen or a sulphonyloxy radical, and

R has the abovementioned meaning, if appropriate in the presence of a base and if appropriate in the presence of a diluent; or d) substituted acetyl-amino acid esters of the general formula (VII)

  (VII)

in which

B, R and $R^5$ have the abovementioned meaning, are reacted with amines of the formula (VIII)

  (VIII)

in which $R^3$ and $R^4$ have the abovementioned meaning, if appropriate in the presence of a diluent and if appropriate in the presence of a base; or e) carboxyl-activated acetyl-amino acids of the general formula (IX)

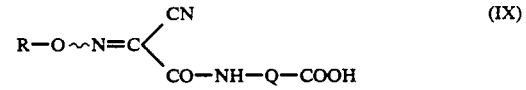  (IX)

in which

R has the abovementioned meaning, and

Q represents A or B, the latter having the above-mentioned meaning, are reacted with compounds of the formula (X)

Y—H  (X)

in which

Y represents the $R^2O-$ or $R^3R^4N-$ groups where $R^2$, $R^3$ and $R^4$ have the abovementioned meaning, if appropriate in the presence of a catalyst and if appropriate in the presence of an acid-binding agent and if appropriate in the presence of a diluent; or f) ammonium salts of 2-cyano-2-oximino-acetic acid of the general formula (XI)

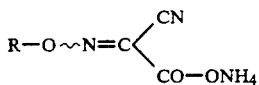

(XI)

in which
R has the abovementioned meaning,
are reacted with aldehydes of the formula (XII)

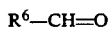

(XII)

in which
the $R^6$—CH= group represents the abovementioned meanings of A or B,
and with isonitriles of the formula (XIII)

(XIII)

in which
$R^4$ has the abovementioned meaning,
if appropriate in the presence of a diluent; or g) 2-cyano-2-oximino-acetic acids of the general formula (IV)

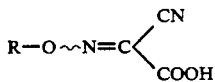

(IV)

in which
R has the abovementioned meaning,
are reacted with isocyanates of the formula (XIV)

$R^1$—NCO (XIV)

in which
$R^1$ has the abovementioned meaning,
if appropriate in the presence of a catalyst and if appropriate in the presence of a diluent; or h) 2-cyano-2-oximino-acetamides of the general formula (XV)

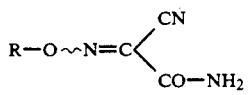

(XV)

in which
R has the abovementioned meaning,
are reacted with a base, if appropriate in the presence of a diluent, and the resultant salts are reacted directly or, if appropriate, after intermediate isolation, with compounds of the formula (XVI)

(XVI)

in which
$R^1$ and X have the abovementioned meaning,
if appropriate in the presence of a diluent.

Finally, it has been found that the new (2-cyano-2-oximinoacetyl)-amino acid derivatives have, inter alia, strong fungicidal properties. In this respect, the compounds according to the invention surprisingly exhibit a stronger action than the substituted 2-cyano-2-methoximinoacetamides known from the prior art, which are similar compounds constitutionally and/or regarding their action. The substances according to the invention thus represent an enrichment of the art.

All aliphatic radicals listed in the description, such as alkyl, alkoxy, alkenyl, inter alia, individually or in compositions, may be straight-chain or branched and the ring systems are likewise monosubstituted or polysubstituted, preferably monosubstituted to pentasubstituted, particularly preferably monosubstituted to trisubstituted, by identical or different substituents, even when not expressly stated.

Halogen denotes fluorine, chlorine, bromine or iodine, preferably fluorine, chlorine and bromine, particularly preferably fluorine and chlorine.

Formula (I) provides a general definition of the (2-cyano-2-oximinoacetyl)-amino acid derivatives according to the invention, where preferably, in the formula (I), R represents straight-chain or branched alkyl having 1 to 4 carbon atoms, straight-chain or branched cyanoalkyl having 1 to 4 carbon atoms in the alkyl part, in each case straight-chain or branched alkenyl or alkinyl having 2 to 6 carbon atoms, cycloalkyl or cycloalkylalkyl each of which has 3 to 6 carbon atoms per cycloalkyl part and 1 to 4 carbon atoms in the straight-chain or branched part and each of which is optionally monosubstituted to pentasubstituted by identical or different alkyl having 1 to 4 carbon atoms, or represents benzyl or phenethyl, each of which is optionally monosubstituted to pentasubstituted by identical or different substituents, phenyl substituents which may be mentioned in each case being: halogen, alkyl or alkoxy in each case having 1 to 4 carbon atoms, halogenoalkyl and halogenoalkoxy in each case having 1 or 2 carbon atoms and 2 to 5 identical or different halogen atoms;

$R^1$ represents the —A—$COOR^2$ or —B—$CONR^3R^4$ groups,

A represents a straight-chain or branched alkylene chain having 1 to 4 carbon atoms, B represents a straight-chain or branched alkylene chain having 1 to 4 carbon atoms, $R^2$ represents monosubstituted or disubstituted, straight-chain or branched alkyl having 1 to 6 carbon atoms, substituents which may preferably be mentioned being: halogen, and phenyl and cycloalkyl which have 3 to 6 carbon atoms and are optionally monosubstituted to pentasubstituted by identical or different substituents from the series comprising halogen, alkyl and alkoxy in each case having 1 to 4 carbon atoms;

$R^3$ represents monosubstituted or disubstituted, straight-chain or branched alkyl having 1 to 4 carbon atoms, substituents which may preferably be mentioned being: halogen, cyano, —$COOR^I$, $CONR^{II}R^{III}$ —$NR^{II}R^{III}$, —$OR^{IV}$, —$S(O)_nR^{IV}$, acyl having 2 to 9 carbon atoms, phenyl which is optionally monosubstituted to pentasubstituted by identical or different substituents from the series comprising halogen and alkyl having 1 to 4 carbon atoms, a 5- or 6-membered heterocyclic ring having 1 to 3 heteroatoms, in particular oxygen, sulphur and nitrogen atoms, which is optionally monosubstituted to pentasubstituted by identical or different substituents from the series comprising halogen and alkyl and alkoxy in each case having 1 to 4 carbon atoms, cycloalkyl having 3 to 6 carbon atoms and cycloalkenyl having 5 to 7 carbon atoms each of which is optionally monosubstituted to pentasubstituted by identical or different alkyl having 1 to 4 carbon atoms;

$R^3$ furthermore preferably represents straight-chain or branched alkenyl or alkinyl in each case having 2 to 6 carbon atoms; cycloalkenyl having 5 to 7 carbon atoms which is optionally monosubstituted to pentasubstituted by identical or different alkyl having 1 to 4 carbon atoms, or cycloalkyl having 3 to 6 carbon atoms which is optionally monosubstituted to pentasubstituted by identical or different substituents, substituents which may preferably be mentioned being: halogen, alkyl and alkoxy in each case having 1 to 4 carbon atoms, cyano, amino, carbamoyl, alkylamino, dialkylamino, alkylcarbamoyl and dialkylcarbamoyl in each case having 1 to 4 carbon atoms in each alkyl part, alkoxycarbonylamino having 1 to 4 carbon atoms in the alkoxy parts, cycloalkyl and cycloalkylalkyl having 5 or 6 carbon atoms in the cycloalkyl part and 1 to 4 carbon atoms in the straight-chain or branched alkyl part, pyrrolidone and phenyl which is optionally monosubstituted to pentasubstituted by identical or different substituents from the series comprising halogen and alkyl having 1 to 4 carbon atoms, $R^3$ additionally preferably represents phenyl which is optionally monosubstituted to pentasubstituted by identical or different substituents from the series comprising halogen, alkyl and alkoxy in each case having 1 to 4 carbon atoms, halogenoalkyl and halogenoalkoxy in each case having 1 or 2 carbon atoms and 1 to 5 identical or different halogen atoms, or represents 5- or 6-membered heterocyclic ring which has 1 to 3 identical or different heteroatoms, such as, in particular, oxygen, sulphur and nitrogen atoms, and which is optionally monosubstituted to pentasubstituted by identical or different substituents, substituents which may be mentioned being halogen, mercapto, phenyl, straight-chain or branched alkyl, alkoxy, alkylthio, alkylsulphinyl and alkylsulphonyl having 1 to 4 carbon atoms per alkyl part;

$R^4$ represents the meanings of $R^3$, represents a polycyclic carbocyclic ring or the $-OR^{IV}$ group, or $R^3$ represents hydrogen or straight-chain or branched alkyl having 1 to 4 carbon atoms, and $R^4$ represents monosubstituted or disubstituted, straight-chain or branched alkyl having 1 to 4 carbon atoms, having the following substituents: acyl having 2 to 9 carbon atoms, hydroxyl, alkylcarbonyloxy having 1 to 4 carbon atoms in the straight-chain or branched alkyl part, $-S(O)_nR^{IV}$, a 5- or 6-membered heterocyclic ring having 1 to 3 heteroatoms, in particular nitrogen, oxygen and sulphur atoms, which is optionally monosubstituted to pentasubstituted by identical or different substituents from the series comprising halogen, straight-chain or branched alkyl and alkoxy in each case having 1 to 4 carbon atoms, cycloalkyl having 3 to 6 carbon atoms and cycloalkenyl having 5 to 7 carbon atoms each of which is optionally monosubstituted to pentasubstituted by identical or different alkyl having 1 to 4 carbon atoms; $R^4$ furthermore represents cycloalkenyl having 5 to 7 carbon atoms which is optionally monosubstituted to pentasubstituted by identical or different, straight-chain or branched alkyl having 1 to 4 carbon atoms, represents a 5- or 6-membered heterocyclic ring having 1 to 3 identical or different heteroatoms, in particular nitrogen, oxygen and sulphur atoms, which is optionally monosubstituted to pentasubstituted by identical or different substituents from the series comprising halogen, mercapto, phenyl, in each case straight-chain or branched alkyl, alkoxy, alkylthio, alkylsulphinyl and alkylsulphonyl having 1 to 4 carbon atoms per alkyl part, represents cycloalkyl having 3 to 6 carbon atoms which is monosubstituted to pentasubstituted by identical or different substituents from the series comprising phenyl, cyano, hydroxyl, alkoxy, alkylamino, dialkylamino, alkylcarbamoyl, dialkylcarbamoyl and alkoxycarbonylamino in each case having 1 to 4 carbon atoms per alkyl part, cycloalkyl and cycloalkylalkyl in each case having 5 to 7 carbon atoms in the cycloalkyl part and 1 to 4 carbon atoms in the alkyl part, where halogen and straight-chain or branched alkyl having 1 to 4 carbon atoms may be mentioned, if appropriate, as additional cycloalkyl substituents, and furthermore represents a polycyclic carbocyclic ring or $-OR^{IV}$, or $R^3$ and $R^4$, together with the nitrogen atom to which they are bound, represent a monocyclic heterocyclic ring which is monosubstituted to pentasubstituted by identical or different substituents, or a bi- or tricyclic heterocyclic ring or spiroheterocyclic ring which is optionally monosubstituted to pentasubstituted by identical or different substituents, heterocyclic rings which may be mentioned being: oxazolidine, pyrrolidine, imidazolidine, piperidine, piperazine, morpholine, thiomorpholine, 1,3-oxazane or 1,3-diazane; these heterocyclic rings may in each case be fused, if appropriate, to 1 or 2 benzene or cyclohexane rings or, if appropriate, bridged by methylene or ethylene.

Substituents which may be mentioned for all heterosystems are:

Straight-chain or branched alkyl and alkoxy in each case having 1 to 4 carbon atoms, cycloalkyl having 3 to 6 carbon atoms, the hydroxyl group or the oxo group, straight-chain or branched alkenyl having 2 to 4 carbon atoms, hydroxycarbonyl, alkoxycarbonyl having 1 to 4 carbon atoms in the straight-chain or branched alkyl part, carbamoyl, alkyl- or dialkylcarbamoyl in each case having 1 to 4 carbon atoms in each alkyl part, and phenyl or phenylalkyl which has 1 to 4 carbon atoms in the straight-chain or branched alkyl part and each of which is optionally monosubstituted or disubstituted by identical or different substituents from the series comprising halogen or straight-chain or branched alkyl and alkoxy in each case having 1 to 4 carbon atoms, $R^I$ represents hydrogen or straight-chain or branched alkyl having 1 to 6 carbom atoms, $R^{II}$ represents hydrogen, straight-chain or branched alkyl having 1 to 6 carbon atoms, phenylalkyl which has 1 to 4 carbon atoms in the straight-chain or branched alkyl part and which is optionally monosubstituted to pentasubstituted by identical or different substituents, phenyl substituents which may be mentioned being: halogen, alkyl and alkoxy in each case having 1 to 4 carbon atoms, halogenoalkyl and halogenoalkoxy in each case having 1 or 2 carbon atoms and 2 to 5 identical or different halogen atoms;

$R^{II}$ furthermore represents alkoxycarbonylalkyl, carbamoylalkyl, alkylcarbamoylalkyl or dialkylcarbamoylalkyl in each case having 1 to 4 carbon atoms in each alkyl part, or cycloalkyl having 3 to 6 carbon atoms which is optionally substituted by straight-chain or branched alkyl having 1 to 4 carbon atoms, $R^{III}$ represents hydrogen, straight-chain or branched alkyl having 1 to 6 carbon atoms, phenylalkyl which has 1 to 4 carbon atoms in the straight-chain or branched alkyl part and which is optionally monosubstituted to pentasubstituted by identical or different substituents, suitable phenyl substituents preferably being the phenyl substituents mentioned in the case of $R^{II}$; $R^{III}$ furthermore represents alkoxycarbonylalkyl, carbamoylalkyl, alkylcarbamoylalkyl or dialkylcarbamoylalkyl in each case having 1 to 4 carbon atoms in each alkyl part, or cycloalkyl having 3 to 6 carbon atoms which is optionally substituted by straight-chain or branched alkyl having 1 to 4 carbon atoms, $R^{IV}$ represent hydrogen, straight-chain or branched alkyl having 1 to 6 carbon atoms, phenylalkyl which has 1 to 4 carbon atoms in the straight-chain or branched alkyl part and which is optionally monosubstituted to pentasubstituted by identical or different substituents, suitable phenyl substituents preferably being the phenyl substituents mentioned in the case of $R^{II}$;

$R^{IV}$ furthermore represents acyl having 2 to 9 carbon atoms, and n represents the numbers 0, 1 or 2.

Particularly preferred (2-cyano-2-oximinoacetyl)-amino acid derivatives of the general formula (I) are those in which R represents alkyl having 1 or 2 carbon atoms, cyanomethyl or cyanoethyl, allyl or propargyl, cyclopropyl, cyclohexyl, cyclopropylmethyl or cyclohexylmethyl which is in each case optionally monosubstituted, disubstituted or trisubstituted by methyl, or benzyl or phenethyl which is in each case optionally monosubstituted, disubstituted or trisubstituted by identical or different substituents from the series comprising halogen and methyl, $R^1$ represents the —B—CONR$^3$R$^4$ group, B represents the —CH$_2$—, —CH(CH$_3$)— or —CH$_2$CH$_2$— groups, $R^3$ represents monosubstituted or disubstituted, straight-chain or branched alkyl having 1 to 4 carbon atoms, substituents which may preferably be mentioned being: halogen, cyano, —COOR$^I$, —CONR$^{II}$R$^{III}$, NR$^{II}$R$^{III}$, —OR$^{IV}$, —S(O)$_n$R$^{IV}$, acyl having 2 to 9 carbom atoms, phenyl which is optionally monosubstituted, disubstituted or trisubstituted by identical or different substituents from the series comprising halogen and alkyl having 1 to 4 carbon atoms, a 5- or 6-membered heterocyclic ring having 1 to 3 identical or different heteroatoms, in particular oxygen, sulphur and nitrogen atoms, which is optionally monosubstituted, disubstituted or trisubstituted by identical or different substituents from the series comprising halogen, straight-chain or branched alkyl and alkoxy in each case having 3 to 6 carbon atoms, and cycloalkyl having 3 to 6 carbon atoms and cycloalkenyl having 5 to 7 carbon atoms each of which is optionally substituted by straight-chain or branched alkyl having 1 to 4 carbon atoms; $R^3$ furthermore particularly preferably represents straight-chain or branched alkenyl or alkinyl in each case having 2 to 6 carbon atoms, cycloalkenyl having 5 to 7 carbon atoms which is optionally substituted by straight-chain or branched alkyl having 1 to 4 carbon atoms, optionally substituted cycloalkyl having 3 to 6 carbon atoms, substituents which may preferably be mentioned being: halogen, straight-chain or branched alkyl and alkoxy in each case having 1 to 4 carbon atoms, cyano, amino, carbamoyl, alkylamino, dialkylamino, alkylcarbamoyl and dialkylcarbamoyl in each case having 1 to 4 carbon atoms in each alkyl part, alkoxycarbonylamino having 1 to 4 carbon atoms in the straight-chain or branched alkoxy part, cycloalkyl and cycloalkylalkyl in each case having 5 or 6 carbon atoms in the cycloalkyl part and 1 to 4 carbon atoms in the straight-chain or branched alkyl part, pyrrolidone or phenyl which is optionally monosubstituted, disubstituted or trisubstituted by identical or different substituents from the series comprising halogen and alkyl having 1 to 4 carbon atoms; $R^3$ furthermore particularly preferably represents phenyl which is optionally monosubstituted disubstituted or trisubstituted by identical or different substituents from the series comprising halogen, straight-chain or branched alkyl and alkoxy in each case having 1 to 4 carbon atoms, halogenoalkyl and halogenoalkoxy in each case having 1 or 2 carbon atoms and 1 to 5 identical or different halogen atoms, or a 5- or 6-membered heterocyclic ring having 1 to 3 identical or different heteroatoms, such as oxygen, sulphur or nitrogen atoms, which is optionally monosubstituted, disubstituted or trisubstituted by identical or different substituents, substituents which may be mentioned being halogen, mercapto, phenyl, straight-chain or branched alkyl, alkoxy, alkylthio, alkylsulphinyl and alkylsulphonyl having 1 to 4 carbon atoms per alkyl part;

$R^4$ represents the meanings of $R^3$, represents a polycyclic carbocyclic ring or the —OR$^{IV}$ group, or $R^3$ represents hydrogen or straight-chain or branched alkyl having 1 to 4 carbon atoms, and $R^4$ represents monosubstituted or disubstituted, straight-chain or branched alkyl having 1 to 4 carbon atoms, having the following substituents; acyl having 2 to 9 carbon atoms, hydroxyl, alkylcarbonyloxy having 1 to 4 carbon atoms in the straight-chain or branched alkyl part, —S(O)$_n$R$^{IV}$, a 5-or 6-membered heterocyclic ring having 1 to 3 heteroatoms, in particular nitrogen, oxygen and sulphur atoms, which is optionally monosubstituted, disubstituted or trisubstituted by identical or different substituents from the series comprising halogen, straight-chain or branched alkyl and alkoxy in each case having 1 to 4 carbon atoms, or cycloalkyl having 3 to 6 carbon atoms and cycloalkenyl having 5 to 7 carbon atoms each of which is optionally monosubstituted, disubstituted or trisubstituted by identical or different alkyl having 1 to 4 carbon atoms;

$R^4$ furthermore represents cycloalkenyl having 5 to 7 carbon atoms which is optionally monosubstituted, disubstituted or trisubstituted by identical or different, straight-chain or branched alkyl having 1 to 4 carbon atoms, represents a 5-or 6-membered heterocyclic ring having 1 to 3 identical or different heteroatoms, in particular nitrogen, oxygen and sulphur atoms, which is optionally monosubstituted, disubstituted or trisubstituted by identical or different substituents from the series comprising halogen, mercapto, phenyl, in each case straight-chain or branched alkyl, alkoxy, alkylthio, alkylsulphinyl and alkylsulphonyl in each case having 1 to 4 carbon atoms per alkyl part, represents cycloalkyl having 3 to 6 carbon atoms which is optionally monosubstituted, disubstituted or trisubstituted by identical or different substituents from the series comprising phenyl, cyano, hydroxyl, alkoxy, alkylamino, dialkylamino, alkylcarbamoyl, dialkylcarbamoyl, alkoxycarbonylamino in each case having 1 to 4 carbon atoms per alkyl part, cycloalkyl and cycloalkylalkyl in each case having 5 to 7 carbon atoms in the cycloalkyl alkyl part and 1 to 4 carbon atoms in the alkyl part, additional cycloalkyl substituents which may be mentioned being, if appropriate, halogen and straight-chain or branched alkyl having 1 to 4 carbon atoms, and furthermore represents a polycyclic carbocyclic ring or —OR$^{IV}$, or $R^3$ and $R^4$, together with the nitrogen atom to which they are bound, represent a monocyclic heterocyclic ring which is monosubstituted, disubstituted or trisubstituted by identical or different substituents, or a bi- or tricyclic heterocyclic ring or spiroheterocyclic ring which is optionally monosubstituted, disubstituted or trisubstituted by identical or different substituents, heterocyclic rings which may be mentioned being: oxazolidine, pyrrolidine, imidazolidine, piperidine, piperazine, morpholine, thiomorpholine, 1,3-oxazane or 1,3-diazane, which heterocyclic rings may in each case be fused, if appropriate, to 1 or 2 benzene or cyclohexane rings or, if appropriate, bridged by methylene or ethylene, substituents which may be mentioned for all heterosystems being:

straight-chain or branched alkyl and alkoxy in each case having 1 to 4 carbon atoms, cycloalkyl having 3 to 6 carbon atoms, the hydroxyl or the oxo group, straight-chain or branched alkenyl having 2 to 4 carbon atoms, hydroxycarbonyl, alkoxycarbonyl having 1 to 4 carbon atoms in the straight-chain or branched alkyl part, carbamoyl, alkyl- and dialkylcarbamoyl in each case having 1 to 4 carbon atoms in each alkyl part, and phenyl or phenylalkyl which has in each case 1 to 4 carbon atoms in the straight-chain or branched alkyl part and each of which is optionally monosubstituted or disubstituted by identical or different substituents from the series comprising halogen or straight-chain or branched alkyl and alkoxy in each case having 1 to 4 carbon atoms, $R^I$ represents hydrogen or straight-chain or branched alkyl having 1 to 4 carbon atoms, $R^{II}$ represents hydrogen, straight-chain or branched alkyl having 1 to 4 carbon atoms, or benzyl or phenethyl each of which is optionally monosubstituted, disubstituted or trisubstituted by identical or different substituents, phenyl substituents which may be mentioned in each case being: fluorine, chlorine, methyl, methoxy and trifluoromethyl; $R^{II}$ furthermore represents alkoxycarbonylalkyl having 1 to 4 carbon atoms in the alkoxy part and 1 or 2 carbon atoms in the alkyl part, carbamoylalkyl having 1 or 2 carbon atoms in the alkyl part, alkylcarbamoylalkyl and dialkylcarbamoylalkyl in each case having 1 or 2 carbon atoms in each alkyl part, or cycloalkyl having 3 to 6 carbon atoms which is optionally monosubstituted, disubstituted or trisubstituted by identical or different substituents from the series comprising methyl and ethyl, $R^{III}$ represents the meanings of $R^{II}$, $R^{IV}$ represents hydrogen, straight-chain or branched alkyl having 1 to 4 carbon atoms, or benzyl or phenethyl each of which is optionally monosubstituted, disubstituted or trisubstituted by identical or different substituents, phenyl substituents which may be mentioned in each case being: fluorine, chlorine, methyl, methoxy and trifluoromethyl; $R^{IV}$ furthermore represents acyl having 2 to 9 carbon atoms, and n represents numbers 0, 1 or 2.

Very particularly preferred (2-cyano-2-oximinoacetyl)-amino acid derivatives of the general formula (I) are those in which (A)

R represents methyl, ethyl, cyanomethyl, cyanoethyl, allyl, propargyl, represents cyclopropyl, cyclohexyl, cyclopropylmethyl or cyclohexylmethyl, each of which is monosubstituted, disubstituted or trisubstituted by methyl, or represents benzyl or phenethyl each of which is optionally monosubstituted, disubstituted or trisubstituted by identical or different substituents from the series comprising halogen and methyl, $R^1$ represents the —B—CO—NR$^3$R$^4$ group, B represents the —CH$_2$—, —CH(CH$_3$)— or —CH$_2$CH$_2$— groups $R^3$ represents monosubstituted or disubstituted alkyl having 1 to 3 carbon atoms, substituents which may be mentioned being: chlorine, hydroxyl, alkylcarbonyloxy having 1 to 4 carbon atoms in the straight-chain or branched alkyl part, alkylcarbonyl having 1 to 4 carbon atoms in straight-chain or branched alkyl part, alkoxy and alkylthio in each case having 1 or 2 carbon atoms, 2-furyl, 2-pyridyl, 1-morpholino, cyclopropyl, cyclohexyl and phenyl which is optionally monosubstituted, disubstituted or trisubstituted by identical or different substituents from the series comprising chlorine and methyl; $R^3$ furthermore very particularly preferably represents allyl or propargyl, 1-cyclohexenyl, or cyclohexyl which is monosubstituted, disubstituted or trisubstituted by identical or different substituents, substituents which may be mentioned being: chlorine, methyl, ethyl, methoxy, cyano, amino, alkyl- and dialkylamino in each case having 1 or 2 carbon atoms in each alkyl part, carbamoyl, alkyl- and dialkylcarbamoyl in each case having 1 or 2 carbon atoms in each alkyl part, cyclohexyl, cyclohexylalkyl having 1 or 2 carbon atoms in the alkyl part and 1-pyrrolidine-2-one;

$R^3$ additionally very particularly preferably represents phenyl which is optionally monosubstituted, disubstituted or trisubstituted by identical or different substituents from the series comprising chlorine and methyl, represents 2-pyridyl or 2-pyrimidinyl each of which is optionally monosubstituted, disubstituted or trisubstituted by methyl, represents 2-thiazolyl which is optionally substituted by phenyl, represents 2-benzothiazolyl which is optionally monosubstituted, disubstituted or trisubstituted by identical or different substituents from the series comprising chlorine, methyl and methoxy, represents 1,2,4-triazol-3-yl, 1,2,4-thiadiazol-5-yl which is optionally substituted by phenyl, represents 1,3,4-thiadiazol-5-yl which is optionally monosubstituted, disubstituted or trisubstituted by identical or different substituents from the series comprising mercapto, straight-chain or branched alkyl having 1 to 4 carbon atoms, in each case straight-chain or branched alkylthio, alkylsulphinyl and alkylsulphonyl in each case having 1 to 4 carbon atoms, or represents the

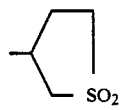

group, $R^4$ represents monosubstituted or disubstituted alkyl having 1 to 3 carbon atoms, substituents which may be mentioned being: chlorine, hydroxyl, alkylcarbonyloxy having 1 to 4 carbon atoms in the straight-chain or branched alkyl part, alkylcarbonyl having 1 to 4 carbon atoms in the straight-chain or branched alkyl part, alkoxy and alkylthio in each case having 1 or 2 carbon atoms, or 2-furyl, 2-pyridyl, 1-morpholino, cyclopropyl, cyclohexyl and phenyl which is optionally monosubstituted, disubstituted or trisubstituted by identical or different substituents from the series comprising chlorine and methyl; $R^4$ furthermore very particularly preferably represents allyl or propargyl, 1-cyclohexenyl, or cyclohexyl which is monosubstituted, disubstituted or trisubstituted by identical or different substituents, substituents which may be mentioned being: chlorine, methyl, ethyl, methoxy, cyano, amino, alkyl- and dialkylamino in each case having 1 or 2 carbon atoms in each alkyl part, carbamoyl, alkyl- and dialkylcarbamoyl in each case having 1 or 2 carbon atoms in each alkyl part, cyclohexyl, cyclohexylalkyl having 1 or 2 carbon atoms in the alkyl part, and 1-pyrrolidin-2-one;

$R^4$ additionally very particularly represents phenyl which is optionally monosubstituted, disubstituted or trisubstituted by identical or different substituents from the series comprising chlorine and methyl, represents 2-pyridyl or 2-pyrimidinyl each of which is optionally monosubstituted, disubstituted or trisubstituted by methyl, represents 2-thiazolyl which is optionally substituted by phenyl, represents 2-benzothiazolyl which is optionally monosubstituted, disubstituted or trisubstituted by identical or different substituents from the series comprising chlorine, methyl and methoxy, represents 1,2,4-triazol-3-yl, represents 1,2,4-thiadiazol-5-yl which is optionally substituted by phenyl, represents 1,3,4-thiadiazol-5-yl which is optionally monosubstituted, disubstituted or trisubstituted by identical or different substituents from the series comprising mercapto, straight-chain or branched alkyl having 1 to 4 carbon atoms in each case straight-chain or branched alkylthio, alkylsulphinyl and alkylsulphonyl in each case having 1 to 4 carbon atoms, or represents the

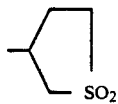

group, $R^4$ furthermore very particularly preferably represents hydroxyl, alkoxy having 1 or 2 carbon atoms, benzyloxy which is optionally monosubstituted, disubstituted or trisubstituted by identical or different substituents from the series comprising chlorine and methyl, 1-adamantyl, 2-norbornyl, 1- or 2-decalyl or 1- or 2-tetralyl, or (B)

R represents methyl, ethyl, cyanomethyl, cyanoethyl, allyl, propargyl, represents cyclopropyl, cyclohexyl, cyclopropylmethyl or cyclohexylmethyl each of which is monosubstituted, disubstituted or trisubstituted by methyl, or represents benzyl or phenethyl each of which is optionally monosubstituted, disubstituted or trisubstituted by identical or different substituents from the series comprising halogen and methyl, $R^1$ represents the —B—CO—NR$^3$R$^4$ group, B represents the —CH$_2$—, —CH(CH$_3$)— or CH$_2$CH$_2$— groups, $R^3$ represents hydrogen or straight-chain or branched alkyl having 1 to 4 carbon atoms, $R^4$ represents substituted alkyl having 1 to 3 carbon atoms, substituents which may be mentioned being: hydroxyl, alkylcarbonyloxy having 1 to 4 carbon atoms in the straight-chain or branched alkyl part, alkylcarbonyl having 1 to 4 carbon atoms in the alkyl part, alkylthio having 1 or 2 carbon atoms, 2-furyl, 2-pyridyl, 1-morpholino, cyclopropyl and cyclohexyl; $R^4$ furthermore very particularly preferably represents 1-cyclohexenyl, represents 2-pyridyl or 2-pyrimidyl each of which is optionally monosubstituted, disubstituted or trisubstituted by methyl, represents 2-thiazolyl which is optionally substituted by phenyl, represents 2-benzothiazolyl which is optionally monosubstituted, disubstituted or trisubstituted by identical or different substituents from the series comprising chlorine, methyl and methoxy, represents 1,2,4-triazol-3-yl, represents 1,2,4-thiadiazol-5-yl which is optionally substituted by phenyl, represents 1,3,4-thiadiazol-5-yl which is optionally monosubstituted, disubstituted or trisubstituted by identical or different substituents from the series comprising mercapto and alkyl, alkylthio, alkylsulphinyl and alkylsulphonyl in each case having 1 to 4 carbon atoms, the

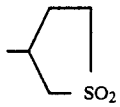

group, 1-adamantyl, 2-norbornyl, 1- or 2-decalyl or 1- or 2-tetralyl; $R^4$ additionally very particularly preferably represents cyclohexyl which is monosubstituted, disubstituted or trisubstituted by identical or different substituents, substituents which may be mentioned being: phenyl, cyano, hydroxyl, alkoxy having 1 or 2 carbon atoms, alkylamino and dialkylamino in each case having 1 or 2 carbon atoms in each alkyl part, alkylcarbamoyl and dialkylcarbamoyl in each case having 1 or 2 carbon atoms in each alkyl part, alkoxycarbonylamino having 1 or 2 carbon atoms in the alkyl part, cyclohexyl, cyclohexylalkyl having 1 or 2 carbon atoms in the alkyl part, and 1-pyrrolidin-2-one, and additionally halogen and alkyl having 1 or 2 carbon atoms, or (C)

R represents methyl, ethyl, cyanomethyl, cyanoethyl, allyl, propargyl, represents cyclopropyl, cyclohexyl, cyclopropylmethyl or cyclohexylmethyl each of which is monosubstituted, disubstituted or trisubstituted by methyl, or represents benzyl or phenethyl each of which is optionally monosubstituted, disubstituted or trisubstituted by identical or different substituents from the series comprising halogen and methyl, $R^1$ represents the —B—CO—NR$^3$N$^4$ group, B represents the —CH$_2$—, —CH(CH$_3$)— or —CH$_2$CH$_2$— groups, $R^3$ and $R^4$, together with the nitrogen atom to which they are bound, represent the following mono-, bi- or tricyclic heterocyclic rings or spiroheterocyclic rings:

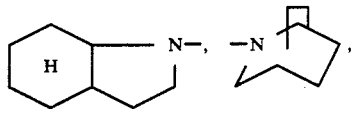

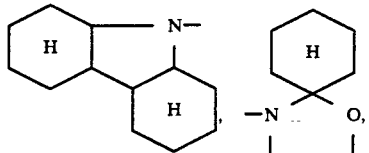

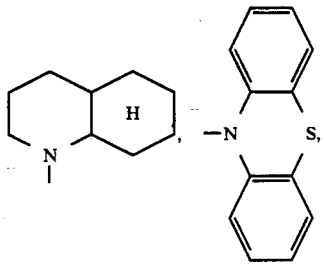

-continued

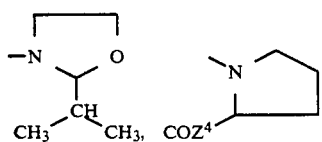
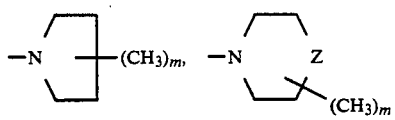
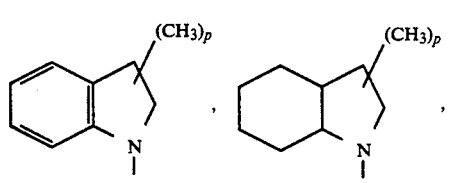
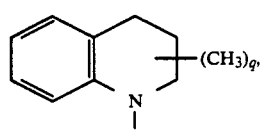
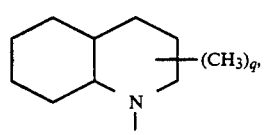
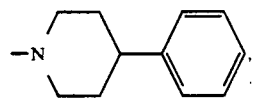
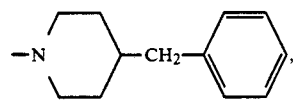
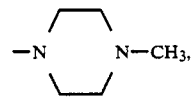
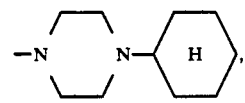
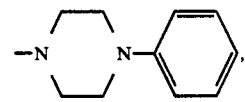
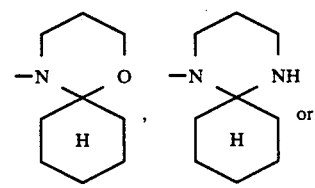

-continued

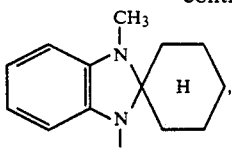

where
Z represents oxygen or the $CH_2$ group,
$Z^4$ represents hydroxyl, methoxy, ethoxy, amino, methylamino, ethylamino, dimethylamino or ethylmethylamino,
m represents the numbers 1, 2, 3 or 4,
p represents numbers 0, 1 or 2, and
q represents the numbers 0, 1, 2 or 3.

The substances of the formula (I) shown in the Table below may be mentioned as examples of compounds according to the invention, in addition to the compounds mentioned in the preparation examples:

$$R-O\sim N=C\begin{matrix}CN\\CO-NH-R^1\end{matrix} \quad (I)$$

| R | $R^1$ |
|---|---|
| $CH_3$ | $-CH_2-CO-N-\left(\underset{H}{\bigcirc}\right)_2$ |
| $CH_3$ | $-CH_2-CO-N-\underset{H}{\bigcirc}$ |
| $CH_3$ | $-CH_2-CO-NH-\underset{H}{\bigcirc}-\bigcirc$ (phenyl) |
| $CH_3$ | $-CH_2-CO-NH\sim\underset{H\;H}{\bigcirc\bigcirc}$ |
| $CH_3$ | $-CH_2-O-NH\sim\bigcirc\bigcirc$ |
| $CH_3$ | $-CH_2-CO-NH\sim\underset{H}{\bigcirc}-NH-CO_2-C_2H_5$ |

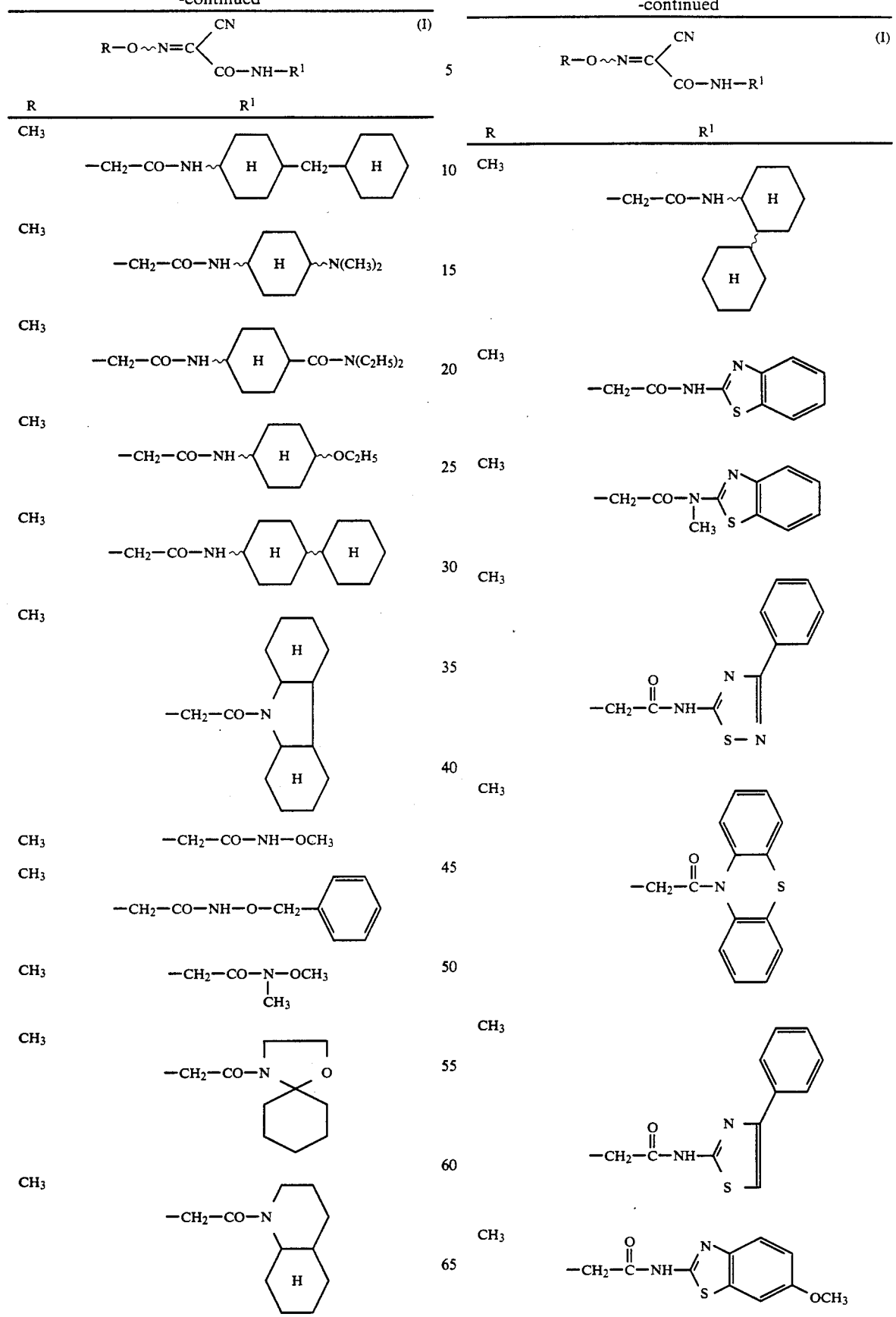

-continued

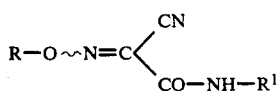  (I)

| R | R¹ |
|---|---|
| CH₃ | 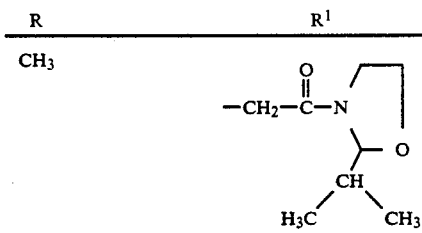 |
| CH₃ | -CH₂-CO-NH-\<N=N-NH\> |

If, for example, ethyl (E)-2-cyano-2-methoximino-acetate and Nα-glycyl-prolinamide hydrobromide are used as starting materials, the course of process (a) according to the invention may be represented by the following equation:

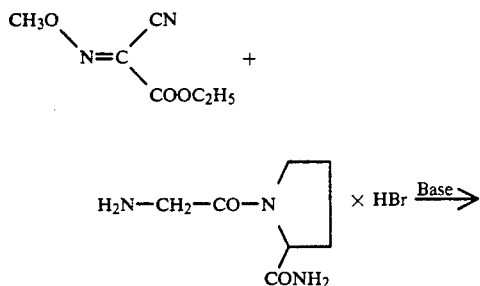

If, for example, (E)-2-cyano-2-methoximino-acetyl chloride and N-glycyl-aminomethylcyclohexane hydrobromide are used as starting materials, the course of process (b) according to the invention may be represented by the following equation:

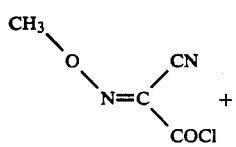

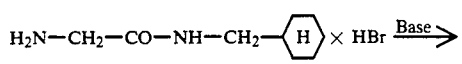

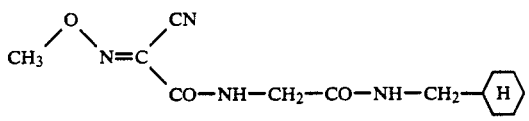

If, for example, the sodium salt of N-cyclohexylmethyl-N'-(2-cyano-2-hydroximinoacetyl)-glycine and dimethyl sulphate are used as starting materials, the course of process (c) according to the invention may be represented by the following equation:

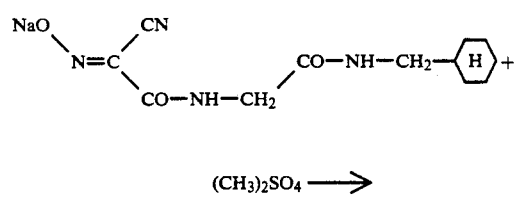

(CH₃)₂SO₄ ⟶

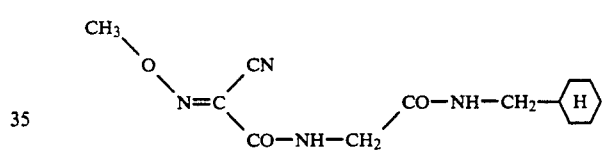

If, for example, N-(2-cyano-2-methoximino-acetyl)-glycine ethyl ester and ethanolamine are used as starting materials, the course of process (d) according to the invention may be represented by the following equation:

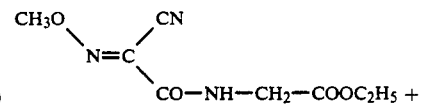

H₂N-CH₂-CH₂-OH ⟶

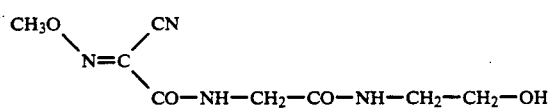

If, for example, N-(2-cyano-2-methoximinoacetyl)-glycine and 4-ethoxycyclohexylamine are used as starting materials and dicyclohexylcarbodiimide and N-hydroxysuccinimide are used as auxiliaries, the course of process (e) according to the invention may be represented by the following equation:

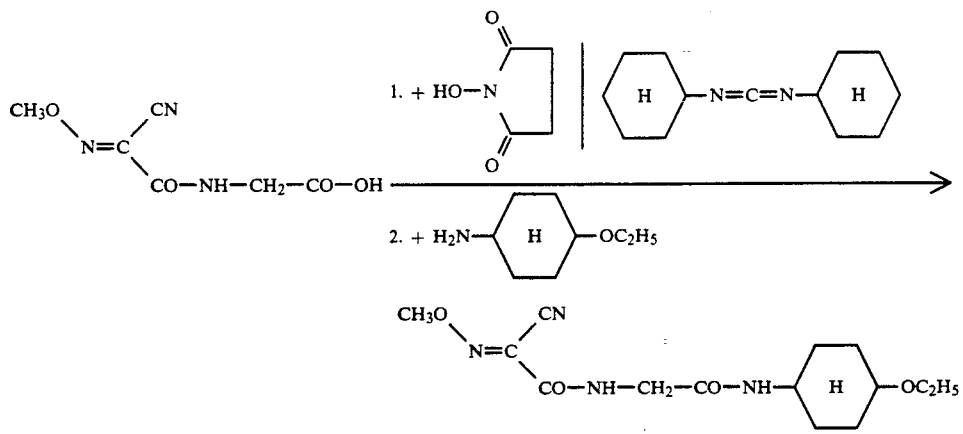

If, for example, the ammonium salt of 2-cyano-2-(benzyloximino)-acetic acid, isobutyraldehyde and cyclohexylmethyl isonitrile are used as starting materials, the course of process (f) according to the invention may be represented by the following equation:

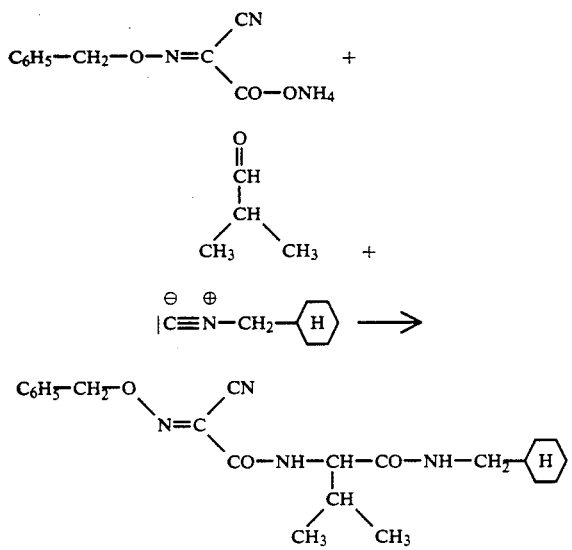

If, for example, 2-cyano-2-(methoximino)-acetic acid and diallylaminocarbonyl-methyl isocyanate are used as starting materials, the course of process (g) according to the invention may be represented by the following equation:

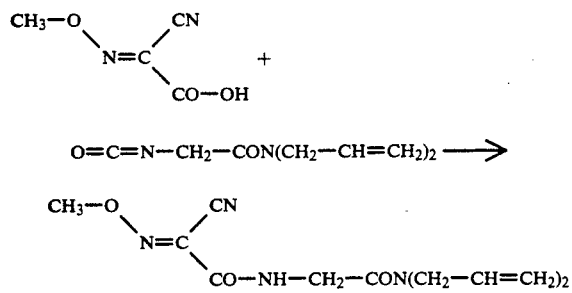

If, for example, 2-cyano-2-(methoximino)-acetamide and N,N-diallyl-bromoacetamide are used as starting materials, the course of process (h) according to the invention may be represented by the following equation:

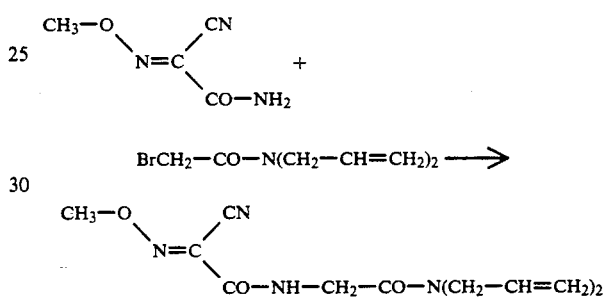

Formula (II) provides a general definition of the 2-cyano-2-oximino-acetates to be used as starting materials for carrying out process (a) according to the invention. In this formula, R preferably has the meaning which has already been mentioned in connection with the description of the substances of the formula (I) according to the invention as being preferred for this substituent. $R^5$ preferably represents methyl or ethyl.

The 2-cyano-2-oximino-acetates of the formula (II) are known (cf., for example, J. Antibiot. 37, 557 (1984); Pesticide Science 12, 27 (1981) and EP-OS (European Published Specification) 0,201,999); or they are the subject-matter of German Patent Applications P 3,625,460 of Jul. 28, 1986, and P 3,625,497 of Jul. 28, 1986 (corresponding respectively to U.S. applications Ser. No. 072,313, filed Jul. 13, 1987, now abandoned, and Ser. No. 072,308, filed Jul. 13, 1987, now abandoned), or they can be obtained in a generally known fashion by the processes given therein.

Formula (III) provides a general definition of the amines additionally to be used as starting materials for carrying out process (a) according to the invention and likewise process (b). In this formula, $R^1$ preferably has the meaning which has already been mentioned in connection with the description of the substances of the formula (I) according to the invention as being preferred for this substituent.

The amines of the formula (III) are known (cf., for example, Houben-Weyl, Methoden der organischen Chemie |Methods of Organic Chemistry|, Volume XV, part 1 and 2, Georg Thieme Verlag, Stuttgart 1974; and R. C. Sheppard, A Specialist Periodical Report, Aminoacids, Peptides and Proteins, The Royal Society of Chemistry, Burlington House, London 1978, and I. P. Greenstein and M. Winitz, Chemistry of Amino Acids, I. Wiley Sons Inc., New York, London 1961; and E. Schröder and K. Lübke, The Peptides Vol. I, Academic Press, New York, London 1965, and EP-OS (European Published Specification) 0,201,999); or they are the subject matter of German Patent Application P 3,625,497, supra, or they can be obtained in a generally known fashion by the processes described therein.

Formula (IV) provides a general definition of the carboxylic acids to be used as starting materials for carrying out process (b) according to the invention and process (g) according to the invention. In this formula, R preferably has the meaning which has already been mentioned in connection with the description of the substances of the formula (I) according to the invention being preferred for this substituent.

Suitable carboxyl-activated derivatives of the carboxylic acids of the formula (IV) are all carboxyl-activated derivatives, such as acyl halides, such as, for example, acyl chlorides, acyl azides, furthermore symmetrical and mixed anhydrides, such as, for example the mixed O-alkylcarbonic anhydrides, furthermore activated esters, such as, for example, p-nitrophenyl esters or N-hydroxysuccinimide esters, and also activated forms of the carboxylic acids which have been generated in situ using condensing agents, such as, for example, dicyclohexylcarbodiimide or carbonyldiimidazole.

The acyl chlorides corresponding to the carboxylic acids of the formula (IV) are preferably employed. They can be prepared by reacting the carboxylic acids of the formula (IV) or salts thereof with a halogenating agent, such as, for example, phosphorus pentachloride, thionyl chloride or oxalyl chloride, in a generally known fashion. The use of oxalyl chloride together with the sodium or potassium salt of the carboxylic acid of the formula (IV) is preferred.

The carboxylic acids of the formula (IV) and the carboxyl-activated derivatives thereof are known (cf., for example, Pesticide Science 12, 27 (1981) and DE-OS (German Published Specification) 3,521,131), or they are the subject-matter of German Patent Applications P 3,602,243 of Jan. 25, 1986, and P 3,625,497, supra, or they can be obtained in a generally known fashion by the processes given therein.

Formula (V) provides a general definition of the 2-cyano-2-oximino-acetamides to be used as starting materials for carrying out process (c) according to the invention. In this formula, $R^1$ preferably has the meaning which has already been mentioned in connection with the description of the substances of the formula (I) according to the invention as being preferred for this substituent. M preferably represents hydrogen or a potassium or sodium equivalent.

Some of the 2-cyano-2-oximino-acetamides of the formula (V) are the subject matter of German Patent Application P 3,702,282 of Jan. 27, 1987 (corresponding to U.S. application Ser. No. 144,895, filed Jan. 15, 1988, now abandoned), or they can be obtained by processes given therein, for example by reacting the cyanoacetate of the formula (XVII)

$$NC-CH_2-CO-OR^7 \qquad (XVII)$$

in which $R^7$ represents methyl or ethyl, with amino acid derivatives of the formula (III)

$$H_2N-R^1 \qquad (III)$$

in which $R^1$ has the abovementioned meaning, if appropriate in the presence of a solvent, such as, for example, methanol, ethanol, diethyl ether, 1,2-dimethoxyethane, dimethylformamide or mixtures thereof with water, at 0° C. to 60° C., preferably at room temperature, and subsequently reacting the compounds of the formula (XVIII)

$$NC-CH_2-CO-NH-R^1 \qquad (XVIII)$$

in which $R^1$ has the abovementioned meaning, thus obtained with nitrous acid or derivatives of nitrous acid, if appropriate in the presence of a diluent, such as, for example, alcohol, and if appropriate in the presence of an acid or a base, such as, for example, hydrogen chloride or an alkali metal alcoholate, at temperatures between −20° C. and 120° C.

The compounds of the formulae (XVII) and (III) are known, or they can be obtained in a generally known fashion.

Formula (VI) provides a general definition of the compounds additionally to be used as starting materials for carrying out process (c) according to the invention. In this formula, R preferably has the meaning which has already been mentioned in connection with the description of the substances of the formula (I) according to the invention as being preferred for this substituent. X preferably represents chlorine, bromine, methylsulphonyloxy or p-toluenesulphonyloxy.

The compounds of the formula (VI) are generally known compounds of organic chemistry, or they can be obtained in a generally known fashion.

Formula (VII) provides a general definition of the substituted acetyl-amino acid esters to be used as starting materials for carrying out process (d) according to the invention. In this formula, B and R preferably have the meanings which have already been mentioned in connection with the description of the substances of the formula (I) according to the invention as being preferred for these substituents. $R^5$ preferably represents methyl or ethyl.

Some of the substituted acetyl-amino acid esters of the general formula (VII) are compounds according to the invention; some of them are known (cf. EP-OS (European Published Specification) 0,201,999 and DE-OS (German Published Specification) 3,521,131), or they are the subject-matter of German Patent Applications P 3,602,243 and P 3,625,497, supra, or they can be obtained by processes given therein.

Formula (VIII) provides a general definition of the amines additionally to be used as starting materials for carrying out process (d) according to the invention. In this formula, $R^3$ and $R^4$ preferably have the meanings which have already been mentioned in connection with the description of the substances of the formula (I) according to the invention as being preferred for these substituents.

The amines of the formula (VIII) are generally known compounds of organic chemistry, or they can be obtained in a generally known fashion.

Formula (IX) provides a general definition of the acetyl-amino acids to be used as starting materials for carrying out process (e) according to the invention. In this formula, R preferably has the meaning which has already been mentioned in connection with the description of the substances of the formula (I) according to the invention as being preferred for this substituent. Q preferably represents the meanings already mentioned in connection with the description of the substances of the formula (I) according to the invention as being preferred for A and B. Suitable carboxyl-activated derivatives are preferably the derivatives already mentioned as being preferred in the case of the carboxylic acids of the formula (IV).

Some of the acetyl-amino acids of the general formula (IX) are compounds according to the invention; some of them are known (cf. EP-OS (European Published Specification) 0.201,999 and DE-OS (German Published Specification) 3,521,131), or they are the subject-matter of German Patent Applications P 3,602,243 and P 3,625,497, supra, or they can be obtained by processes given therein.

Formula (X) provides a general definition of the compounds additionally to be used as starting materials for carrying out process (e) according to the invention. In this formula, Y preferably represents the $R^2O-$ and $R^3R^4N-$ groups, where $R^2$, $R^3$ and $R^4$ preferably have the meanings which have already been mentioned in connection with the description of the substances of the formula (I) according to the invention as being preferred for these substituents.

The compounds of the formula (X) are generally known compounds of organic chemistry, or they can be obtained in a generally known fashion.

Formula (XI) provides a general definition of the ammonium salts of 2-cyano-2-oximino-acetic acids to be used as starting materials for carrying out process (f) according to the invention. In this formula, R preferably has the meaning which has already been mentioned in connection with the description of the substances of the formula (I) according to the invention as being preferred for this substituent.

The ammonium salts of 2-cyano-2-oximino-acetic acids are obtained by reacting the carboxylic acids of the formula (IV) with ammonia in a conventional fashion.

Formula (XII) provides a general definition of the aldehydes additionally to be used as starting materials for carrying out process (f) according to the invention and formula (XIII) provides a general definition of the isonitriles. In the formula (XII), the $R^6-CH=$ group represents the meanings of A and B, these preferably having the meanings which have already been mentioned in connection with the description of the substances of the formula (I) according to the invention as being preferred for these substituents. In the formula (XIII), $R^4$ preferably has the meaning which has already been mentioned in connection with the description of the substances of the formula (I) according to the invention as being preferred for this substituent.

The aldehydes of the formula (XII) and the isonitriles of the formula (XIII) are generally known compounds of organic chemistry, or they can be obtained in a generally known fashion.

Formula (XIV) provides a general definition of the isocyanates to be used as starting materials for carrying process (g) according to the invention. In this formula, $R^1$ preferably has the meaning which has already been mentioned in connection with the description of the substances of the formula (I) according to the invention as being preferred for this substituent.

The isocyanates of the formula (XIV) are generally known compounds of organic chemistry, or they can be obtained in a generally known fashion.

Formula (XV) provides a general definition of the 2-cyano-2-oximino-acetamides to be used as starting materials for carrying out process (h) according to the invention. In this formula, R preferably has the meaning which has already been mentioned in connection with the description of the substances of the formula (I) according to the invention as being preferred for this substituent.

The 2-cyano-2-oximino-acetamides of the formula (XV) are known (cf., for example, Chem. Ber. 54, 1342 (1921); DE-OS (German Published Specification) 2,623,847 and DE-OS (German Published Specification) 2,657,145); or they are the subject-matter of a patent application by the applicant (cf. German Patent Application P 3,702,283 of Jan. 27, 1987, corresponding to U.S. application Ser. No. 146,051, filed Jan. 20, 1988, now U.S. Pat. No. 4,841,086), or they can be obtained by the processes described therein.

The bases furthermore to be used as starting materials for carrying out process (h) according to the invention include all conventional inorganic and organic bases, such as, in particular, alkali metal alcoholates, such as, for example, potassium tert.-butylate; alkali metal hydroxides and carbonates, such as, for example sodium hydroxide, potassium hydroxide and potassium carbonate, and tetraalkylammonium and benzyltrialkylammonium hydroxides and alcoholates, such as, for example, tetramethylammonium hydroxide and alcoholate, tetrabutylammonium hydroxide and alcoholate or benzyltriethylammonium hydroxide and alcoholate.

The bases are generally known compounds of organic chemistry.

Formula (XVI) provides a general definition of the compounds additionally to be used as starting materials for carrying out process (h) according to the invention. In this formula, $R^1$ preferably has the meaning which has already been mentioned in connection with the description of the substances of the formula (I) according to the invention as being preferred for this substituent. X preferably represents chlorine, bromine, methylsulphonyloxy or p-toluenesulphonyloxy.

The compounds of the formula (XVI) are generally known compounds of organic chemistry; or they can be obtained in a generally known fashion.

Suitable diluents for carrying out processes (a) and (d) according to the invention are water and organic solvents. These preferably include alcohols, such as methanol, ethanol or isopropanol; ethers, such as tetrahydrofuran or 1,2-dimethoxyethane; amides, such as dimethylformamide; nitriles, such as acetonitrile, and tertiary amines, such as pyridine.

Processes (a) and (d) according to the invention are carried out, if appropriate, in the presence of a base, depending on whether the particular amines are employed in the form of acid-addition salts. Suitable in this case are conventional organic and inorganic bases. Tert. amines, such as triethylamine; alcoholates, such as sodium methylate, and alkali metal carbonates, such as potassium carbonates, may preferably be mentioned.

When carrying out processes (a) and (d) according to the invention, the temperatures may be varied within a relatively wide range. In general, the processes are carried out at temperatures between $-20°$ C. and the reflux temperature, preferably at room temperature.

When carrying out processes (a) and (d) according to the invention, all reactants may be employed in excess; equimolar amounts are preferably used. The reaction is carried out and the reaction products of the formula (I) are worked up and isolated in a generally conventional fashion.

Suitable diluents for processes (b) and (e) according to the invention are inert organic solvents. These include ketones, such as acetone or ethyl methyl ketone; esters, such as ethyl acetate or methyl acetate; amides, such as dimethylformamide; nitriles, such as acetonitrile; chlorinated hydrocarbons, such as methylene chloride or carbon tetrachloride; hydrocarbons, such as toluene; or ethers, such as tetrahydrofuran; or mixtures thereof.

Suitable acid-binding agents for processes (b) and (e) according to the invention are conventional inorganic and organic acid binders. These preferably include tertiary amines, such as triethylamine, pyridine or N-methylmorpholine, and inorganic bases, such as sodium carbonate or calcium carbonate.

Processes (b) and (e) according to the invention are carried out, if appropriate, in the presence of a catalyst. Examples which may be mentioned are 4-dimethylaminopyridine, 1-hydroxy-benzotriazole or dimethylformamide.

When carrying out processes (b) and (e), the temperatures may be varied within a relatively wide range. In general, the processes are carried out at temperatures between −60° C. and +120° C., preferably at −20° C. to +40° C.

When carrying out processes (b) and (e) according to the invention, equimolar amounts are preferably used. The reaction is carried out and the reaction products of the formula (I) are worked up and isolated in a generally conventional fashion.

Suitable diluents for process (c) according to the invention are organic solvents. These include alcohols, such as methanol and ethanol; ketones, such as acetone and methyl isobutyl ketone; nitriles, such as acetonitrile; esters, such as ethyl acetate; ethers, such as tetrahydrofuran; amides, such as dimethylformamide and N-methylpyrrolidone, and also dimethyl sulphoxide.

Suitable bases for process (c) according to the invention are all conventional organic and inorganic bases. These preferably include tertiary amines, such as triethylamine, pyridine and 1,8-diazabicyclo|5,4,0|-undec-7-ene (DBU), and inorganic bases, such as sodium carbonate, potassium carbonate or calcium carbonate.

When carrying out process (c) according to the invention, the reaction temperatures may be varied within a relatively wide range. In general, the process is carried out at temperatures between 0° C. and 150° C., preferably at temperatures between 20° C. and 120° C.

When carrying out process (c) according to the invention, 1 to 3 mols, preferably 1 to 2 mols, of the compound of the formula (VI) are generally employed per mol of 2-cyano-2-oximino-acetamide of the formula (V). The reaction is carried and the reaction products of the formula (I) are worked up and isolated in a generally conventional fashion. It should be emphasized that the 2-cyano-2-oximino-acetamides of the formula (V) can be further reacted directly after their preparation without isolation.

Suitable diluents for process (f) according to the invention are all conventional organic solvents. These preferably include alcohols, such as methanol or ethanol; ethers, such as diethyl ether; chlorinated hydrocarbons, such as chloroform or carbon tetrachloride; and ketones, such as acetone.

When carrying out process (f) according to the invention, the temperatures may be varied within a relatively wide range. In general, the process is carried out at temperatures between −20° C. and +40° C., preferably at 0° to 20° C.

When carrying out process (f) according to the invention, equimolar amounts are preferably used. The reaction is carried out and the reaction products of the formula (I) are worked up and isolated in a generally conventional fashion.

Suitable diluents for process (g) according to the invention are inert organic solvents. These include aromatic hydrocarbons, such as toluene; chlorinated hydrocarbons, such as methylene chloride; ethers, such as tetrahydrofuran or 1,2-dimethoxyethane; esters, such as ethyl acetate; and nitriles, such as acetonitrile.

Process (g) according to the invention is carried out, if appropriate, in the presence of a catalyst. Examples which may be mentioned are triethylamine, 1,4-diazabicyclo[2,2,2]octane (DABCO) and 1,8-diazabicyclo[5,4,0]undec-7-ene (DBU).

When carrying out process (g) according to the invention, the temperatures may be varied within a relatively wide range. In general, the process is carried out at temperatures between −20° C. and the reflux temperature, preferably at room temperature.

When carrying out process (g) according to the invention, all reactants may be employed in a slight excess; equimolar amounts are preferably used. The reaction is carried out and the reaction products of the formula (I) according to the invention are worked up and isolated in a generally conventional fashion.

Suitable diluents for process (h) according to the invention are inert organic solvents. Ethers, such as diethyl ether, diisopropyl ether, tetrahydrofuran or dioxane; ketones, such as acetone or methyl ethyl ketone; furthermore acetonitrile and dimethylformamide may preferably be used.

When carrying out process (h) according to the invention, the reaction temperatures may be varied within a relatively wide range. The salt formation is generally carried out at temperatures between 0° C. and 100° C., preferably between 0° C. and 30° C. The subsequent alkylation is generally carried out at temperatures between 0° C. and 150° C., preferably between 60° C. and 120° C.

When carrying out process (h) according to the invention, equimolar amounts are preferably employed, if appropriate an excess of up to 1 mol of the alkylating agent of the formula (XVI). The salts of the compounds of the formula (XV) may be isolated, if desired, but the process can be carried out without isolation. In some cases, it proves advantageous to initially convert the acetamides of the formula (XV) into an alkali metal salt and then to convert the latter into the corresponding ammonium salt using tetraalkylammonium or benzyltrialkylammonium chlorides or bromides. The reaction is carried out and the reaction products of the formula (I) are worked up and isolated in a generally conventional fashion.

The active compounds according to the invention have a strong microbicidal action and can be employed in practice for combating undesired microorganisms. The active compounds are suitable for use as pesticides, above all as fungicides.

For example, fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera Leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Pseudocercosporella species, such as, for example, *Pseudocercosporella herpotrichoides*.

The good toleration, by plants, of the active compounds, at the concentrations required for combating plant diseases, permits treatment of above-ground parts of plants, of vegatative propagation stock and seeds, and of the soil.

As pesticides, the active compounds according to the invention can be employed particularly successfully for combating Phytophthora species, such as, for example, *Phytophthora infestans*, on tomatoes; and also for combating Plasmopara species, such as, for example, *Plasmopara viticola*, on vines.

It should be particularly emphasized that the active compounds according to the invention not only exhibit a protective action, but also have a curative action, i.e. on application after contamination with the spores of the fungus.

Furthermore, the active compounds according to the invention are very highly suitable for combating Pyricularia species, such as *Pyricularia oryzae*, on rice.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

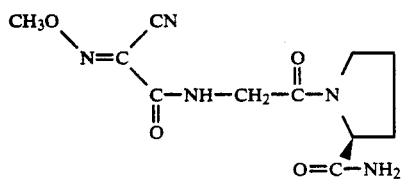

Process a 8.0 g (79.2 mmol) of triethylamine are added dropwise at 0° C. to a solution of 6.45 g (39.6 mmol) of 96 percent strength ethyl (E)-2-cyano-2-methoximino-acetate and 10.0 g (39.6 mmol) of Nα-glycyl-L-prolinamide hydrobromide in 45 ml of absolute methanol, and the mixture is stirred at room temperature for 21 hours. The mixture is diluted with 160 ml of diethyl ether, the precipitate is filtered off under suction, the filtrate is evaporated in vacuo, and the residue is chromatographed on a silica gel column (5×50 cm) using MeOH/CHCl₃ (0–70%).

4.56 g of a fraction which, besides the desired product, also contains triethylamine hydrobromide are thus obtained. The latter is removed from the aqueous solution using Lewatite S 100, H+ form. After evaporating the solution and drying the residue, 3.2 g (29% of theory) of Nα-{N-[(E)-2-cyano-2-methoximinoacetyl]-glycyl}-L-prolinamide of melting point 90°–94° C. are thus obtained.

Preparation of the starting material

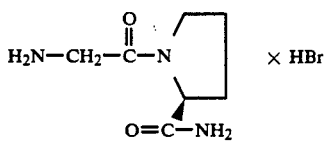

A mixture of 13 g (0.043 mol) of Nα-(N-benzyloxycarbonyl-glycyl)-L-prolinamide and 55 ml of a 33 percent solution of hydrogen bromide in glacial acetic acid is stirred at room temperature for 4 hours. 350 ml of ether are added, and the precipitate is filtered off under suction, washed with ethyl acetate and petroleum ether, and dried in vacuo over potassium hydroxide.

10 g (92% of theory) of Nα-glycyl-L-prolinamide hydrobromide of melting point 120° C.–122° C. (decomposition) are obtained.

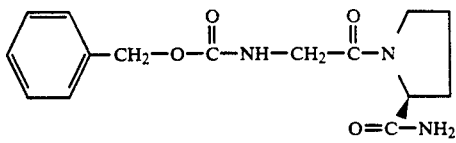

Ammonia is passed into a solution of 34.2 g (0.106 mol) of Nα-(N-benzyloxycarbonyl-glycyl)-L-proline methyl ester in 150 ml of methanol at 0° C. until saturation is achieved, and the mixture is allowed to stand at room temperature for 3 days. Ammonia is then again passed in at 0° C. After a total of 5 days at room temperature, 500 ml of absolute ether are added, a precipitate being produced after trituration. The latter is filtered off under suction, washed with ether and dried.

15.7 g (49% of theory) of Nα-(N-benzyloxycarbonyl-glycyl)-prolinamide of melting point 142° C. to 143° C. are obtained.

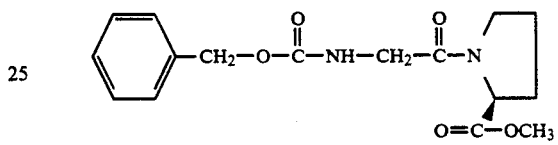

27.6 g (0.2 mol) of isobutyl chloroformate are added dropwise to a solution of 41.9 g (0.2 mol) of N-benzyloxycarbonyl-glycine and 19.8 g (0.2 mol) of N-methylpiperidine in 250 ml of dry methylene chloride at −20° C. After the solution has been stirred at −20° C. for 10 minutes, a pre-cooled solution of 33.2 g (0.2 mol) of L-proline methyl ester hydrochloride and 19.8 g (0.2 mol) of N-methylpiperidine in 100 ml of dry methylene chloride is added in one portion at −60° C., and the mixture is stirred at −15° C. for 2 hours and at room temperature for 3 days.

The reaction solution is washed with 1M citric acid (2×100 ml), saturated sodium hydrogen carbonate solution (2×100 ml) and water (2×100 ml), dried over sodium sulphate and evaporated.

57.0 g (89% of theory) of N-(N-benzyloxycarbonyl-glycyl)-L-proline methyl ester are obtained as a yellowish oil.

Example 2

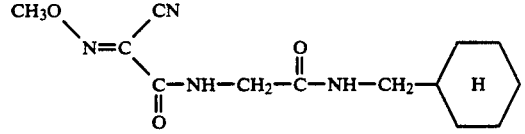

Process b 11.1 g (0.11 mol) of triethylamine and, at 0° C., 7.4 g (0.05 mol) of (E)-2-cyano-2-methoximinoacetyl chloride are added dropwise to a solution of 12.6 g (0.05 mol) of N-glycylaminomethylcyclohexane hydrobromide in 100 ml of dry dimethylformamide. The mixture is stirred at 0° C. for 1 hour and at room temperature for 17 hours.

The reaction mixture is evaporated in vacuo, the residue is dissolved in 250 ml of toluene and 50 ml of methylene chloride, and the solution is washed with 100 ml each of 1M hydrochloric acid, saturated sodium hydrogen carbonate solution and saturated sodium chloride solution, and dried over sodium sulphate.

The mixture is filtered, the filtrate is evaporated, and the residue is crystallized from ethyl acetate (50 ml)/petroleum ether (180 ml), and 5.4 g (39% of theory) of N-{N-[(E)-2-cyano-2-methoximinoacetyl]-glycyl}-aminomethylcyclohexane of melting point 90° C.-92° C. are obtained.

Preparation of the starting material of the formula (IV)

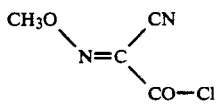

20 g (0.12 mol) of the potassium salt of (E)-2-cyano-2-methoximinoacetic acid are suspended in 250 ml of dry ether, and, after addition of a few drops of dimethylformamide, 76.2 g (0.6 mol) of oxalyl chloride are added dropwise at 0° C. The reaction mixture is stirred at 0° C. for 2 hours, and filtered. The filtrate is evaporated in vacuo at room temperature, and the mixture is freed from the oxalyl chloride which remains by evaporating twice with methylene chloride.

13.5 g (77% of theory) of (E)-2-cyano-2-methoximinoacetyl chloride are obtained as a yellow oil which is immediately reacted further.

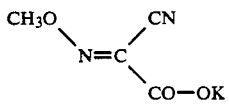

A solution of 45.1 g (0.806 mol) of potassium hydroxide in 500 ml of water is added dropwise to a solution of 124.8 g (0.672 mol) of 84 percent strength ethyl (E)-2-cyano-2-methoximino-acetate in 500 ml of ethanol at 20° C., and the reaction mixture is stirred at 40° C. for 1 hour. The solution is evaporated in vacuo at 40° C., and the mixture is stirred with methanol for 30 minutes, filtered off under suction, washed with ethanol, acetonitrile and dichloromethane and dried at room temperature.

58.6 g (53% of theory) of the potassium salt of (E)-2-cyano-2-methoximino-acetic acid are obtained.

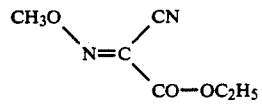

161 g (1.25 mol) of dimethyl sulphate (98% purity) are added dropwise over the course of 30 minutes to a suspension of 164 g (1 mol) of ethyl (E)-2-cyano-2-hydroximino-acetate, sodium salt (G. Kinast, Liebigs Ann. Chem., 1981, 1561), and 138 g of powdered potassium carbonate in 1.5 liters of acetone, and the reaction mixture is refluxed for 3 hours. After cooling, the mixture is filtered through kieselguhr, and the solution is evaporated. 124.8 g (68% of theory) of ethyl (E)-2-cyano-2-methoximino-acetate are obtained as a red-brown oil of 85% purity (GC). After chromatography on five times the amount of silica gel 60 using chloroform, a 93 percent purity pale yellow oil is obtained.

Preparation of the starting material of the formula (III)

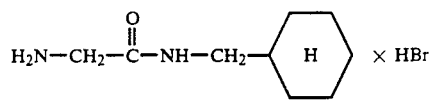

54.8 g (0.18 mol) of N-(N-benzyloxycarbonyl-glycyl)-aminomethylcyclohexane are dissolved in 200 ml of 33 percent hydrogen bromide in glacial acetic acid, and the mixture is stirred at room temperature for 3 hours. After diluting the mixture with 150 ml of absolute ether, the precipitate is filtered off under suction, washed with absolute ether and dried in a desiccator over potassium hydroxide.

44.8 g (99% of theory) of N-glycyl-aminomethylcyclohexane hydrobromide, which melts at 205° C.-207° C. with decomposition, are obtained.

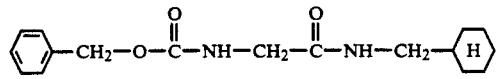

19.8 g (0.2 mol) of pre-cooled N-methylpiperidine and 27.6 g (0.2 mol) of pre-cooled isobutyl chloroformate are added dropwise to a suspension of 41.9 g (0.2 mol) of N-benzyloxycarbonyl-glycine in 250 ml of methylene chloride at −20° C., the mixture is stirred at −20° C. for 10 minutes, and, after the mixture has been cooled to −60° C., a solution of 22.7 g (0.2 mol) of aminomethylcyclohexane in 50 ml of methylene chloride is added in one portion. The temperature is allowed to rise to −15° C., and the mixture is stirred at −15° C. for 2 hours, and at room temperature for 17 hours. The reaction solution is washed twice each with 100 ml each of 1M hydrochloric acid, saturated sodium hydrogen carbonate solution and saturated sodium chloride solution, dried over sodium sulfate and evaporated in vacuo.

59.7 g (98% of theory) of N-(N-benzyloxycarbonyl-glycyl)-aminomethylcyclohexane of melting point 95° C.-98° C. are obtained.

Example 3

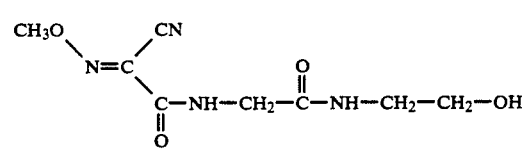

Process d 18.0 g (0.3 mol) of ethanolamine are added to a solution of 22.5 g (0.1 mol) of 95 percent purity N-[(E)-2-cyano-2-methoximino-acetyl]-glycine ethyl ester in 200 ml of isopropanol at 20° C., and the mixture is stirred at room temperature for 15 hours. After 200 ml of ether have been added, the precipitate is filtered off under suction, washed with ether and dried. 22.4 g (98% of theory) of N-{N-[(E)-2-cyano-2-methoximinoacetyl]-glycyl}ethanolamine of melting point 145° C.-148° C. are obtained.

Example 4

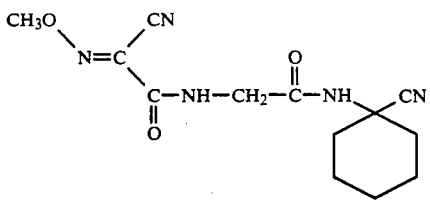

Process e

A solution of 10.4 g (0.05 mol) of N,N'-dicyclohexylcarbodiimide in 25 ml of dry dimethylformamide is added dropwise to a solution of 9.25 g (0.05 mol) of N-[(E)-2-cyano-2-methoximino-acetyl]-glycine and 5.95 g (0.05 mol) of N-hydroxysuccinimide in 50 ml of dry dimethylformamide at 0° C., and the solution is stirred at 0° C. for 1 hour. A solution of 8.05 g (0.05 mol) of 1-cyanocyclohexylamine hydrochloride in 75 ml of dry dimethylformamide and 5.05 g (0.05 mol) of triethylamine are then added dropwise at 0° C., and the mixture is stirred at room temperature for 20 hours.

The precipitate (dicyclohexylurea) is filtered off under suction and washed with dimethylformamide. The combined filtrates are evaporated, the residue is dissolved in methylene chloride, and the solution is washed with sodium hydrogen carbonate solution, 1M hydrochloric acid and water, dried and evaporated. After crystallization from chloroform/petroleum ether, 8.7 g (60% of theory) of 1-Nα-[(E)-2-cyano-2-methoximino-acetyl]-glycinamidocyclohexyl cyanide of melting point 151° C.-153° C. are obtained.

Preparation of the starting materials

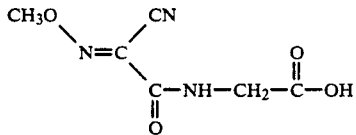

47.2 g (0.22 mol) of N-[(E)-2-cyano-2-methoximino-acetyl]-glycine ethyl ester and 35.6 g (0.11 mol) of barium hydroxide octahydrate are stirred for 3 hours at room temperature in 50 ml of water and 100 ml of ethanol. The mixture is evaporated in vacuo at 40° C., the residue is washed with ether and dissolved in 400 ml of water, and 6.2 ml (0.11 mol) of concentrated sulphuric acid are added with ice cooling. The precipitated barium sulphate is filtered off, the filtrate is evaporated in vacuo, and the residue is dried.

31 g (76% of theory) of N-[(E)-2-cyano-2-methoximino-acetyl]-glycine of melting point 95° C.-100° C. are obtained.

Example 5

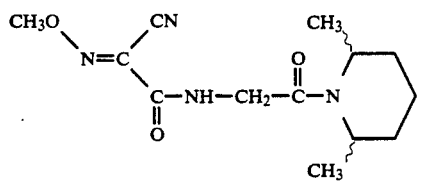

Process h 11.6 g (0.05 mol) of benzyltriethylammonium chloride are suspended in 50 ml of absolute tetrahydrofuran, 11.5 g (0.05 mol) of 26 percent strength methanolic sodium methylate solution are added, and the mixture is evaporated in vacuo. A solution of 6.35 g (0.05 mol) of (E)-2-cyano-2-methoximino-acetamide in 150 ml of absolute tetrahydrofuran and a solution of 9.5 g (0.05 mol) of N-chloroacetyl-2,6-dimethylpiperidine in 50 ml of absolute tetrahydrofuran are added to the residue. The mixture is refluxed for 5 hours and stirred at room temperature for 16 hours. The residue which remains after removal of the solvent by distillation is triturated in 200 ml of ice water, and the precipitate is filtered off under suction, dried and recrystallized from ethyl acetate/petroleum ether.

7.05 g (50% of theory) of N-{N-[(E)-2-cyano-2-methoximino-acetyl)-glycyl}-2,6-dimethylpiperidine of melting point 125° C.-126° C. are obtained.

The (2-cyano-2-oximinoacetyl)-amino acid derivatives of the general formula (I) below are obtained in an analogous fashion and in accordance with processes (a) to (h) according to the invention:

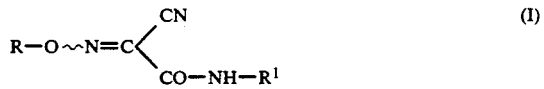

| Ex. No. | R | R¹ | m.p. °C. |
|---|---|---|---|
| 6 | CH₃— | —CH₂—CO—NH—⟨cyclic SO₂⟩ | 157–158 (E isomer) |
| 7 | CH₃ | —CH₂—CO—NH—⟨pyridyl⟩ | 155–156 (E isomer) |
| 8 | CH₃— | —CH₂—CO—NH—CH₂CH₂—O—COCH₃ | 110–114 (E isomer) |

-continued $$R-O\sim N=C\begin{matrix}CN\\CO-NH-R^1\end{matrix} \quad (I)$$

| Ex. No. | R | R¹ | m.p. °C. |
|---|---|---|---|
| 9 | CH₃— | —CH₂—CO—N⟨pyrrolidine-2-COOCH₃⟩ (L) | 139–141 (E isomer) |
| 10 | CH₃— | —CH₂—CO—N⟨pyrrolidine-2-CONHCH₃⟩ (L) | 181–183 (E isomer) |
| 11 | CH₃ | —CH₂—CO—N⟨pyrrolidine-2-COOH⟩ (L) | 65–72 (E-isomer) |
| 12 | CH₃ | —CH₂—CO—N⟨norbornyl⟩ | 120–122 (E-isomer) |
| 13 | CH₃ | —CH₂—CO—NH—(decahydronaphthyl, H,H) | 129–131 (E-isomer) |
| 14 | CH₃ | —CH₂—CO—NH—CH₂—(2-furyl) | 93–95 (E-isomer) |
| 15 | CH₃ | —CH₂—CO—N(CH₂—CH=CH₂)₂ | 67–68 (E-isomer) |
| 16 | CH₃ | —CH₂—CO—NH—(adamantyl) | 213–214 (E-isomer) |
| 17 | CH₃ | —CH₂—CO—N—(cyclohexyl-H)₂ | 150 (decomp.) (E-isomer) |
| 18 | CH₃ | —CH₂—CO—NH~(cyclohexyl,H)~N(2-oxopyrrolidinyl) | 237–39 |

-continued $$\underset{R-O\sim N=C}{\overset{CN}{\underset{CO-NH-R^1}{}}} \quad (I)$$

| Ex. No. | R | R¹ | m.p. °C. |
|---|---|---|---|
| 19 | CH₃ | —CH₂—CO—NH—(1,2,3,4-tetrahydronaphthalen-1-yl) | 135–37 |
| 20 | CH₃ | —CH₂—CO—NH—(pyrimidin-2-yl) | 210–12 |
| 21 | CH₃ | —CH₂—CO—NH—(1,2,4-triazol-3-yl) | 252–54 |
| 22 | CH₃ | —CH₂—CO—NH—(4-methylpyrimidin-2-yl) | 205–06 |
| 23 | CH₃ | —CH₂—CO—NH—(thiazol-2-yl) | 219–20 |
| 24 | CH₃ | —CH₂—CO—N(2,6-dimethylmorpholin-4-yl) | 169–70 |
| 25 | CH₃ | —CH₂—CO—NH—[2-(cyclohex-1-enyl)cyclohexyl] | 104–06 |
| 26 | CH₃ | —CH₂—CO—NH—(trans-4-(NH—COOC₂H₅)cyclohexyl) | 220–22 |
| 27 | CH₃ | —CH₂—CO—NH—(trans-4-(CO—N(C₂H₅)₂)cyclohexyl) | 228–30–(decomp.) |

-continued $$R-O\sim N=C\begin{smallmatrix}CN\\CO-NH-R^1\end{smallmatrix} \quad (I)$$

| Ex. No. | R | R¹ | m.p. °C. |
|---|---|---|---|
| 28 | CH₃ | 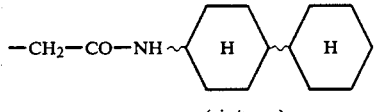 —CH₂—CO—NH~[cyclohexyl-H]—[cyclohexyl-H] (cis/trans) | 179–81 |
| 29 | CH₃ | 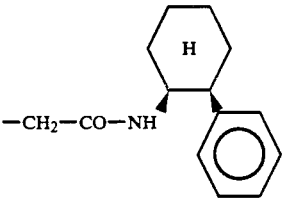 —CH₂—CO—NH—[cyclohexyl-H, phenyl] (cis) | 141–43 |
| 30 | CH₃ | 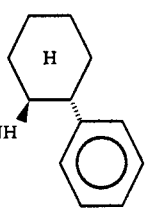 —CH₂—CO—NH—[cyclohexyl-H, phenyl] (trans) | 181–83 |
| 31 | CH₃ | 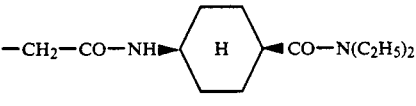 —CH₂—CO—NH—[cyclohexyl-H]—CO—N(C₂H₅)₂ (cis) | 160–65 |
| 32 | CH₃ | 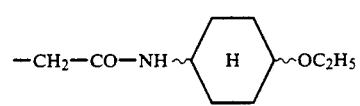 —CH₂—CO—NH~[cyclohexyl-H]~OC₂H₅ (cis/trans) | 172–74 |
| 33 | CH₃ | 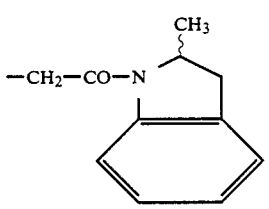 —CH₂—CO—N[indoline with CH₃] | 157–60 |
| 34 | CH₃ | 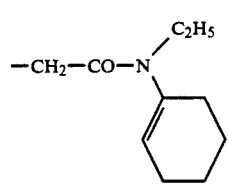 —CH₂—CO—N(C₂H₅)(cyclohexenyl) | 86–88 |
| 35 | CH₃ | 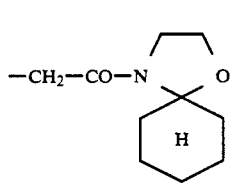 —CH₂—CO—N[1-oxa-4-cyclohexyl spiro, H] | 165–70 (E-isomer) |

-continued $$R-O\sim N=C\begin{matrix}CN\\CO-NH-R^1\end{matrix} \quad (I)$$

| Ex. No. | R | R¹ | m.p. °C. |
|---|---|---|---|
| 36 | CH₃ | —CH₂—CO—NH—[norbornyl] (exo) | 129–31 (E-isomer) |
| 37 | CH₃ | —CH₂—CO—N[piperidine-4-CH₂-phenyl] | 112–14 (E-isomer) |
| 38 | CH₃ | —CH₂—CO—N(CH₂—phenyl)₂ | 97–100 (E-isomer) |
| 39 | CH₃— | —CH₂—CO—N[3,5-dimethylmorpholine] | 167–69 (E-isomer) |
| 40 | CH₃ | —CH₂—CO—N[dicyclohexyl-H,H] | 110–13 (E-isomer) |
| 41 | CH₃ | —CH₂—CO—N(CH₃)(cyclohexenyl) | 128–30 (E-isomer) |
| 42 | CH₃ | —CH₂—CO—N[decahydroquinolinyl,H] | 80–83 (E-isomer) |
| 43 | CH₃ | —CH₂—CO—NH—O—CH₂—phenyl | 116–17 (E-isomer) |
| 44 | CH₃ | —CH₂—CO—N—(—CH₂—C≡CH)₂ | 115–16 (E-isomer) |
| 45 | CH₃ | —CH₂—CO—N(C₂H₅)(CH₂-furyl) | viscous oil (E-isomer) |

-continued

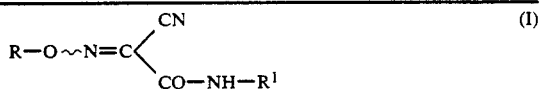

| Ex. No. | R | R¹ | m.p. °C. |
|---|---|---|---|
| 46 | $CH_3$ | $-CH_2-CO-N-[-(CH_2)_3-O-(CH_2)_2OCH_3]_2$ | viscous oil (E-isomer) |
| 47 | $CH_3$ | $-CH_2-CO-N-(-CH_2CH_2OCH_3)_2$ | 55-57 (E-isomer) |
| 48 | $CH_3$ | $-CH_2-CO-N\begin{smallmatrix}C_2H_5\\OC_2H_5\end{smallmatrix}$ | 133-36 (E-isomer) |
| 49 | $CH_3$ | $-CH_2-CO-N$ (bicyclic H group) | viscous oil (E-isomer) |

USE EXAMPLES

In the following use examples, the compounds shown below are employed as comparison substances:

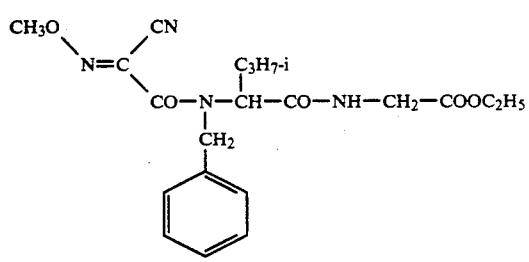 (A)

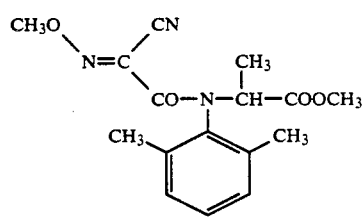 (B)

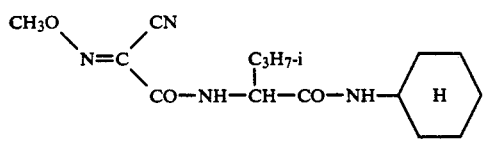 (C)

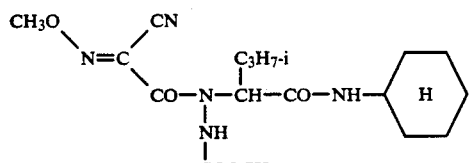 (D)

(known from DE-OS (German Published Specification) 3,521,131)

Example A

Phytophthora Test (tomato)/curative
Solvent: 5.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of Phytophthora infestans. The plants remain in an incubation cabin at 20° C. and 100% relative atmospheric humidity for 7 hours. After a short drying off time, the plants are sprayed with the preparation of active compound until dripping wet.

The plants are placed in an incubation cabin at 100% relative atmospheric humidity and at about 20° C.

Evaluation is carried out 3 days after the inoculation.

In this test, for example, a clearly superior activity compared to the prior art is exhibited by the compounds of preparation Examples 7 and 9.

Example B

Plasmopara test (vines)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, for example a clearly superior activity compared to the prior art is exhibited by the compounds of preparation Examples 2 and 7.

It will be understood that the specification and examples are illustrative but not limitative of the present invention and that other embodiments within the spirit and scope of the invention will suggest themselves to those skilled in the art.

What is claimed is:

1. A (2-cyano-2-oximinoacetyl)-amino derivative of the formula

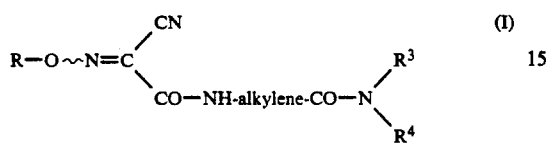

in which
R represents straight-chain or branched alkyl having 1 to 4 carbon atoms;
represents straight-chain or branched cyanoalkyl having 1 to 4 carbon atoms in the alkyl part;
represents in each case straight-chain or branched alkenyl or alkinyl having 2 to 6 carbon atoms;
represents cycloalkyl or cycloalkylalkyl each of which has 3 to 6 carbon atoms per cycloalkyl part and 1 to 4 carbon atoms in the straight-chain or branched alkyl part and each of which is unsubstituted or monosubstituted to pentasubstituted by identical or different alkyl having 1 to 4 carbon atoms; or
represents benzyl or phenethyl, each of which is unsubstituted or monosubstituted to pentasubstituted on phenyl by a substituent independently selected from the group consisting of halogen, alkyl or alkoxy in each case having 1 to 4 carbon atoms, and halogenoalkyl and halogenoalkoxy in each case having 1 or 2 carbon atoms and 2 to 5 identical or different halogen atoms;
"alkylene" represents a straight-chain or branched alkylene chain having 1 to 4 carbon atoms;
$R^3$ represents hydrogen or alkyl having 1 to 4 carbon atoms;
$R^4$ represents alkyl having 1 to 4 carbon atoms, which is monosubstituted or disubstituted by a substituent independently selected from the group consisting of:
(a) alkylcarbonyl having 1 to 4 carbon atoms in the straight-chain or branched alkyl part;
(b) hydroxyl;
(c) $-S(O)_nR^{IV}$;
(d) cycloalkyl having 3 to 6 carbon atoms and which is unsubstituted or monosubstituted to pentasubstituted by identical or different $C_{1-4}$-alkyl; and
(e) cycloalkenyl having 5 to 7 carbon atoms and which is unsubstituted or monosubstituted to pentasubstituted by identical or different $C_{1-4}$-alkyl;
represents cycloalkenyl having 5 to 7 carbon atoms, which is unsubstituted or monosubstituted to pentasubstituted by identical or different $C_{1-4}$-alkyl; or
represents $-OR^{IV}$;
$R^{IV}$ represents hydrogen;
represents straight-chain or branched alkyl having 1 to 6 carbon atoms; or
represents phenylalkyl, which has 1 to 4 carbon atoms in the straight-chain or branched alkyl part and which is unsubstituted or monosubstituted to pentasubstituted in the phenyl part by a substituent independently selected from the group consisting of halogen, alkyl or alkoxy each having 1 to 4 carbon atoms, and halogenoalkyl and halogenoalkoxy in each case having 1 or 2 carbon atoms and 2 to 5 identical or different halogen atoms; and
n represents 0, 1 or 2.

2. A (2-cyano-2-oximinoacetyl)-amino derivative according to claim 1, in which
R represents methyl or ethyl;
represents cyanomethyl or cyanoethyl;
represents allyl or propargyl;
represents cyclopropyl, cyclohexyl, cyclopropylmethyl or cyclohexylmethyl, each of which is monosubstituted, disubstituted or trisubstituted by methyl; or
represents benzyl or phenethyl, each of which is unsubstituted or monosubstituted to trisubstituted on phenyl by a substituent independently selected from the group consisting of halogen and methyl.

3. The compound

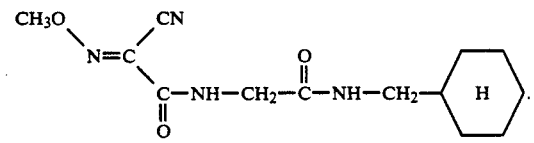

4. A fungicidal composition comprising a fungicidally effective amount of a compound according to claim 1 and a diluent.

5. A method of combating fungi which comprises applying to such fungi or to a fungus habitat a fungicidally effective amount of a compound according to claim 1.

6. A method of combating fungi which comprises applying to such fungi or to a fungus habitat a fungicidally effective amount of a compound represented by the formula

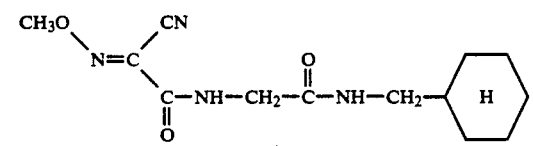

* * * * *